(12) United States Patent
Saliman et al.

(10) Patent No.: US 8,449,533 B2
(45) Date of Patent: May 28, 2013

(54) DEVICES, SYSTEMS AND METHODS FOR MENISCUS REPAIR

(75) Inventors: Justin D. Saliman, Los Angeles, CA (US); Alexander Jasso, Portland, OR (US); George V. Anastas, San Carlos, CA (US)

(73) Assignee: Ceterix Orthopaedics, Inc., Menlo Park, CA (US)

( * ) Notice: Subject to any disclaimer, the term of this patent is extended or adjusted under 35 U.S.C. 154(b) by 0 days.

(21) Appl. No.: 13/462,728

(22) Filed: May 2, 2012

(65) Prior Publication Data

US 2012/0265221 A1 Oct. 18, 2012

Related U.S. Application Data

(63) Continuation of application No. 12/942,803, filed on Nov. 9, 2010.

(60) Provisional application No. 61/259,572, filed on Nov. 9, 2009, provisional application No. 61/295,354, filed on Jan. 15, 2010, provisional application No. 61/318,215, filed on Mar. 26, 2010.

(51) Int. Cl.
*A61B 17/00* (2006.01)

(52) U.S. Cl.
USPC .......................................................... 606/1

(58) Field of Classification Search
None
See application file for complete search history.

(56) References Cited

U.S. PATENT DOCUMENTS

| | | | |
|---|---|---|---|
| 1,037,864 | A | 9/1912 | Carlson et al. |
| 1,815,725 | A | 7/1931 | Pilling et al. |
| 2,738,790 | A | 3/1956 | Todt, Sr. et al. |
| 3,470,875 | A | 10/1969 | Johnson |
| 4,021,896 | A | 5/1977 | Stierlein |
| 4,109,658 | A | 8/1978 | Hughes |
| 4,164,225 | A | 8/1979 | Johnson et al. |

(Continued)

FOREIGN PATENT DOCUMENTS

| EP | 0647431 A2 | 4/1995 |
|---|---|---|
| SU | 376089 A | 4/1973 |

(Continued)

OTHER PUBLICATIONS

Arthrex®, Arthrex, Inc., "The Next Generation in Shoulder Repair Technology," Product Brochure from Arthrex, Inc; Naples, Florida, 2007 (month unavailable), 22 pages.

(Continued)

*Primary Examiner* — Melanie Tyson
*Assistant Examiner* — Son Dang
(74) *Attorney, Agent, or Firm* — Shay Glenn LLP

(57) ABSTRACT

Described herein are meniscus suture passers for repair of the meniscus of the knee. These devices are typically suture passers that may include an elongate body having a pair of arms. One or more of the arms may be angled or bent at the distal end region relative to the long axis of the device, forming a distal-facing opening that is configured to fit meniscus tissue. One or both arms may be movable in the axial direction (e.g., the direction of the long axis of the device). The devices typically include a tissue penetrating element housed within one of the arms but configured to extend across the distal opening between the arms. Thus, a suture may be passed from a first side of the tissue to a second side.

25 Claims, 36 Drawing Sheets

U.S. PATENT DOCUMENTS

| | | | |
|---|---|---|---|
| 4,236,470 A | 12/1980 | Stenson | |
| 4,345,601 A | 8/1982 | Fukuda | |
| 4,440,171 A | 4/1984 | Nomoto et al. | |
| 4,484,580 A | 11/1984 | Nomoto et al. | |
| 4,605,002 A * | 8/1986 | Rebuffat | 606/148 |
| 4,621,640 A | 11/1986 | Mulhollan et al. | |
| 4,706,666 A | 11/1987 | Sheets | |
| 4,836,205 A | 6/1989 | Barrett | |
| 4,923,461 A | 5/1990 | Caspari et al. | |
| 4,957,498 A | 9/1990 | Caspari et al. | |
| 5,002,561 A | 3/1991 | Fisher | |
| 5,011,491 A | 4/1991 | Boenko et al. | |
| 5,059,201 A | 10/1991 | Asnis | |
| 5,129,912 A | 7/1992 | Noda et al. | |
| 5,156,608 A * | 10/1992 | Troidl et al. | 606/142 |
| 5,193,473 A | 3/1993 | Asao et al. | |
| 5,211,650 A | 5/1993 | Noda | |
| 5,222,962 A | 6/1993 | Burkhart | |
| 5,250,053 A | 10/1993 | Snyder | |
| 5,250,055 A * | 10/1993 | Moore et al. | 606/148 |
| 5,254,126 A | 10/1993 | Filipi et al. | |
| 5,330,488 A | 7/1994 | Goldrath | |
| 5,336,229 A | 8/1994 | Noda | |
| 5,342,389 A | 8/1994 | Haber et al. | |
| 5,368,601 A | 11/1994 | Sauer et al. | |
| 5,389,103 A | 2/1995 | Melzer et al. | |
| 5,391,174 A * | 2/1995 | Weston | 606/148 |
| 5,397,325 A | 3/1995 | Della Badia et al. | |
| 5,431,666 A | 7/1995 | Sauer et al. | |
| 5,437,681 A | 8/1995 | Meade et al. | |
| 5,454,823 A | 10/1995 | Richardson et al. | |
| 5,474,057 A | 12/1995 | Makower et al. | |
| 5,478,344 A | 12/1995 | Stone et al. | |
| 5,478,345 A | 12/1995 | Stone et al. | |
| 5,480,406 A | 1/1996 | Nolan et al. | |
| 5,496,335 A | 3/1996 | Thomason et al. | |
| 5,499,991 A | 3/1996 | Garman et al. | |
| 5,507,757 A | 4/1996 | Sauer et al. | |
| 5,520,702 A | 5/1996 | Sauer et al. | |
| 5,522,820 A | 6/1996 | Caspari et al. | |
| 5,540,704 A | 7/1996 | Gordon et al. | |
| 5,540,705 A | 7/1996 | Meade et al. | |
| 5,562,686 A | 10/1996 | Sauer et al. | |
| 5,569,301 A | 10/1996 | Granger et al. | |
| 5,571,090 A | 11/1996 | Sherts | |
| 5,571,119 A | 11/1996 | Atala | |
| 5,575,800 A | 11/1996 | Gordon | |
| 5,578,044 A | 11/1996 | Gordon et al. | |
| 5,616,131 A | 4/1997 | Sauer et al. | |
| 5,618,290 A | 4/1997 | Toy et al. | |
| 5,626,588 A | 5/1997 | Sauer et al. | |
| 5,632,751 A | 5/1997 | Piraka | |
| 5,643,289 A | 7/1997 | Sauer et al. | |
| 5,645,552 A | 7/1997 | Sherts | |
| 5,669,917 A | 9/1997 | Sauer et al. | |
| 5,674,229 A | 10/1997 | Tovey et al. | |
| 5,674,230 A | 10/1997 | Tovey et al. | |
| 5,681,331 A | 10/1997 | de la Torre et al. | |
| 5,690,652 A | 11/1997 | Wurster et al. | |
| 5,709,708 A | 1/1998 | Thal | |
| 5,713,910 A | 2/1998 | Gordon et al. | |
| 5,728,107 A | 3/1998 | Zlock et al. | |
| 5,728,113 A | 3/1998 | Sherts | |
| 5,741,278 A | 4/1998 | Stevens | |
| 5,749,879 A | 5/1998 | Middleman et al. | |
| 5,755,728 A | 5/1998 | Maki | |
| 5,759,188 A | 6/1998 | Yoon | |
| 5,766,183 A | 6/1998 | Sauer | |
| 5,792,153 A | 8/1998 | Swain et al. | |
| 5,800,445 A | 9/1998 | Ratcliff et al. | |
| 5,814,054 A | 9/1998 | Kortenbach et al. | |
| 5,824,009 A | 10/1998 | Fukuda et al. | |
| 5,843,100 A | 12/1998 | Meade | |
| 5,843,126 A | 12/1998 | Jameel | |
| 5,876,412 A | 3/1999 | Piraka | |
| 5,895,395 A | 4/1999 | Yeung | |
| 5,897,563 A | 4/1999 | Yoon et al. | |
| 5,899,911 A | 5/1999 | Carter | |
| 5,899,920 A | 5/1999 | DeSatnick et al. | |
| 5,906,630 A | 5/1999 | Anderhub et al. | |
| 5,908,428 A | 6/1999 | Scirica et al. | |
| 5,935,138 A | 8/1999 | McJames, II et al. | |
| 5,938,668 A | 8/1999 | Scirica et al. | |
| 5,944,739 A | 8/1999 | Zlock et al. | |
| 5,947,982 A | 9/1999 | Duran | |
| 5,980,538 A | 11/1999 | Fuchs et al. | |
| 5,993,466 A | 11/1999 | Yoon | |
| 6,048,351 A | 4/2000 | Gordon et al. | |
| 6,051,006 A | 4/2000 | Shluzas et al. | |
| 6,053,933 A | 4/2000 | Balazs et al. | |
| 6,056,771 A | 5/2000 | Proto | |
| 6,071,289 A | 6/2000 | Stefanchik et al. | |
| 6,077,276 A | 6/2000 | Kontos | |
| 6,099,550 A | 8/2000 | Yoon | |
| 6,126,666 A | 10/2000 | Trapp et al. | |
| 6,129,741 A | 10/2000 | Wurster et al. | |
| 6,139,556 A | 10/2000 | Kontos | |
| 6,159,224 A | 12/2000 | Yoon | |
| 6,190,396 B1 | 2/2001 | Whitin et al. | |
| 6,217,592 B1 | 4/2001 | Freda et al. | |
| 6,221,085 B1 | 4/2001 | Djurovic | |
| 6,238,414 B1 | 5/2001 | Griffiths | |
| 6,277,132 B1 | 8/2001 | Brhel | |
| 6,322,570 B1 | 11/2001 | Matsutani et al. | |
| 6,325,808 B1 | 12/2001 | Bernard et al. | |
| 6,332,889 B1 | 12/2001 | Sancoff et al. | |
| 6,355,050 B1 | 3/2002 | Andreas et al. | |
| 6,368,334 B1 | 4/2002 | Sauer | |
| 6,443,963 B1 | 9/2002 | Baldwin et al. | |
| 6,454,778 B2 | 9/2002 | Kortenbach | |
| 6,511,487 B1 | 1/2003 | Oren et al. | |
| 6,533,795 B1 | 3/2003 | Tran et al. | |
| 6,533,796 B1 | 3/2003 | Sauer et al. | |
| 6,551,330 B1 | 4/2003 | Bain et al. | |
| 6,585,744 B1 | 7/2003 | Griffith | |
| 6,605,096 B1 | 8/2003 | Ritchart | |
| 6,626,917 B1 | 9/2003 | Craig | |
| 6,626,929 B1 | 9/2003 | Bannerman | |
| 6,638,283 B2 | 10/2003 | Thal | |
| 6,638,286 B1 * | 10/2003 | Burbank et al. | 606/157 |
| 6,641,592 B1 | 11/2003 | Sauer et al. | |
| 6,719,764 B1 | 4/2004 | Gellman et al. | |
| 6,719,765 B2 | 4/2004 | Bonutti | |
| 6,723,107 B1 | 4/2004 | Skiba et al. | |
| 6,770,084 B1 | 8/2004 | Bain et al. | |
| 6,896,686 B2 | 5/2005 | Weber | |
| 6,921,408 B2 | 7/2005 | Sauer | |
| 6,923,806 B2 | 8/2005 | Hooven et al. | |
| 6,923,819 B2 | 8/2005 | Meade et al. | |
| 6,936,054 B2 | 8/2005 | Chu | |
| 6,984,237 B2 | 1/2006 | Hatch et al. | |
| 6,991,635 B2 | 1/2006 | Takamoto et al. | |
| 6,997,931 B2 | 2/2006 | Sauer et al. | |
| 6,997,932 B2 | 2/2006 | Dreyfuss et al. | |
| 7,004,951 B2 | 2/2006 | Gibbens, III | |
| 7,029,480 B2 | 4/2006 | Klein et al. | |
| 7,029,481 B1 | 4/2006 | Burdulis, Jr. et al. | |
| 7,041,111 B2 | 5/2006 | Chu | |
| 7,063,710 B2 | 6/2006 | Takamoto et al. | |
| 7,087,060 B2 | 8/2006 | Clark | |
| 7,112,208 B2 | 9/2006 | Morris et al. | |
| 7,118,583 B2 | 10/2006 | O'Quinn et al. | |
| 7,131,978 B2 | 11/2006 | Sancoff et al. | |
| 7,166,116 B2 | 1/2007 | Lizardi et al. | |
| 7,175,636 B2 | 2/2007 | Yamamoto et al. | |
| 7,211,093 B2 | 5/2007 | Sauer et al. | |
| 7,232,448 B2 | 6/2007 | Battles et al. | |
| 7,235,086 B2 | 6/2007 | Sauer et al. | |
| 7,311,715 B2 | 12/2007 | Sauer et al. | |
| 7,344,545 B2 | 3/2008 | Takemoto et al. | |
| 7,390,328 B2 | 6/2008 | Modesitt | |
| 7,442,198 B2 | 10/2008 | Gellman et al. | |
| 7,481,817 B2 | 1/2009 | Sauer | |
| 7,491,212 B2 | 2/2009 | Sikora et al. | |
| 7,588,583 B2 | 9/2009 | Hamilton et al. | |
| 7,594,922 B1 | 9/2009 | Goble et al. | |
| 7,608,084 B2 | 10/2009 | Oren et al. | |

| | | |
|---|---|---|
| 7,632,284 B2 | 12/2009 | Martinek et al. |
| 7,674,276 B2 | 3/2010 | Stone et al. |
| 7,731,727 B2 | 6/2010 | Sauer |
| 7,736,372 B2 | 6/2010 | Reydel et al. |
| 7,749,236 B2 | 7/2010 | Oberlaender et al. |
| 7,842,050 B2 | 11/2010 | Diduch et al. |
| 7,879,046 B2 | 2/2011 | Weinert et al. |
| 7,883,519 B2 | 2/2011 | Oren et al. |
| 7,918,868 B2 * | 4/2011 | Marshall et al. .............. 606/144 |
| 7,938,839 B2 | 5/2011 | DiFrancesco et al. |
| 7,951,147 B2 | 5/2011 | Privitera et al. |
| 7,951,157 B2 | 5/2011 | Gambale |
| 7,951,159 B2 | 5/2011 | Stokes et al. |
| 7,972,344 B2 | 7/2011 | Murray et al. |
| 8,177,795 B2 * | 5/2012 | Niese et al. ................... 606/144 |
| 2003/0023250 A1 | 1/2003 | Watschke et al. |
| 2003/0065337 A1 | 4/2003 | Topper et al. |
| 2003/0078599 A1 | 4/2003 | O'Quinn et al. |
| 2003/0204194 A1 | 10/2003 | Bittar |
| 2003/0216755 A1 | 11/2003 | Shikhman et al. |
| 2003/0233106 A1 | 12/2003 | Dreyfuss |
| 2004/0249392 A1 | 12/2004 | Mikkaichi et al. |
| 2004/0249394 A1 | 12/2004 | Morris et al. |
| 2004/0267304 A1 | 12/2004 | Zannis et al. |
| 2005/0033319 A1 | 2/2005 | Gambale et al. |
| 2005/0033365 A1 | 2/2005 | Courage |
| 2005/0080434 A1 | 4/2005 | Chung et al. |
| 2005/0090837 A1 | 4/2005 | Sixto et al. |
| 2005/0090840 A1 | 4/2005 | Gerbino et al. |
| 2005/0154403 A1 | 7/2005 | Sauer et al. |
| 2005/0288690 A1 * | 12/2005 | Bourque et al. .............. 606/144 |
| 2006/0020272 A1 | 1/2006 | Gildenberg |
| 2006/0047289 A1 | 3/2006 | Fogel |
| 2006/0084974 A1 | 4/2006 | Privitera et al. |
| 2006/0106423 A1 | 5/2006 | Weisel et al. |
| 2007/0032799 A1 | 2/2007 | Pantages et al. |
| 2007/0149986 A1 * | 6/2007 | Morris et al. ................. 606/144 |
| 2007/0156150 A1 | 7/2007 | Fanton et al. |
| 2007/0250118 A1 | 10/2007 | Masini |
| 2007/0260260 A1 | 11/2007 | Hahn et al. |
| 2008/0027468 A1 | 1/2008 | Fenton et al. |
| 2008/0086147 A1 | 4/2008 | Knapp |
| 2008/0091219 A1 | 4/2008 | Marshall et al. |
| 2008/0097489 A1 | 4/2008 | Goldfarb et al. |
| 2008/0140091 A1 | 6/2008 | DeDeyne et al. |
| 2008/0228204 A1 | 9/2008 | Hamilton et al. |
| 2008/0234725 A1 | 9/2008 | Griffiths et al. |
| 2008/0243147 A1 | 10/2008 | Hamilton et al. |
| 2008/0269783 A1 | 10/2008 | Griffith |
| 2009/0012538 A1 | 1/2009 | Saliman et al. |
| 2009/0018554 A1 | 1/2009 | Thorne et al. |
| 2009/0062819 A1 | 3/2009 | Burkhart et al. |
| 2009/0105751 A1 | 4/2009 | Zentgraf |
| 2009/0131956 A1 | 5/2009 | Dewey et al. |
| 2009/0209998 A1 | 8/2009 | Widmann |
| 2009/0228041 A1 | 9/2009 | Domingo |
| 2009/0306684 A1 | 12/2009 | Stone et al. |
| 2010/0057109 A1 | 3/2010 | Clerc et al. |
| 2010/0106169 A1 | 4/2010 | Niese et al. |
| 2010/0114137 A1 | 5/2010 | Vidal et al. |
| 2010/0121352 A1 | 5/2010 | Murray et al. |
| 2010/0130990 A1 | 5/2010 | Saliman |
| 2010/0145364 A1 | 6/2010 | Keren et al. |
| 2010/0185232 A1 | 7/2010 | Hughett et al. |
| 2010/0198235 A1 | 8/2010 | Pierce et al. |
| 2010/0228271 A1 | 9/2010 | Marshall et al. |
| 2010/0241142 A1 | 9/2010 | Akyuz et al. |
| 2010/0249806 A1 | 9/2010 | Oren et al. |
| 2010/0249809 A1 | 9/2010 | Singhatat et al. |
| 2010/0256656 A1 | 10/2010 | Park |
| 2010/0280530 A1 | 11/2010 | Hashiba |
| 2010/0305581 A1 | 12/2010 | Hart |
| 2010/0305583 A1 | 12/2010 | Baird et al. |
| 2010/0331863 A2 | 12/2010 | Saliman |
| 2011/0028998 A1 | 2/2011 | Adams et al. |
| 2011/0060350 A1 | 3/2011 | Powers et al. |
| 2011/0087246 A1 | 4/2011 | Saliman et al. |
| 2011/0112555 A1 | 5/2011 | Overes et al. |
| 2011/0112556 A1 | 5/2011 | Saliman |
| 2011/0118760 A1 | 5/2011 | Gregoire et al. |
| 2011/0130773 A1 | 6/2011 | Saliman et al. |
| 2011/0152892 A1 | 6/2011 | Saliman et al. |
| 2011/0190815 A1 | 8/2011 | Saliman |
| 2011/0218557 A1 | 9/2011 | Saliman |
| 2011/0251626 A1 | 10/2011 | Wyman et al. |
| 2011/0270280 A1 | 11/2011 | Saliman |

FOREIGN PATENT DOCUMENTS

| | | |
|---|---|---|
| SU | 7288848 A1 | 4/1980 |
| SU | 1725847 A1 | 4/1992 |
| WO | WO 98/31288 A1 | 7/1998 |
| WO | WO 03/028532 A2 | 4/2003 |
| WO | WO 03/077771 A1 | 9/2003 |
| WO | WO 2005/037112 A1 | 4/2005 |
| WO | WO 2006/001040 A1 | 1/2006 |
| WO | WO 2006/007399 A1 | 1/2006 |
| WO | WO 2010/036227 A1 | 4/2010 |
| WO | WO 2010/050910 A1 | 5/2010 |
| WO | WO 2010/141695 A1 | 12/2010 |

OTHER PUBLICATIONS

ArthroCare® Sportsmedicine, Sunnyvale, CA, SmartStitch® Suture Passing System with the PerfectPasserTM, Product brochure, 2006 (month unavailble), 4 pages.

BiPass(TM) Suture Punch, Biomet® Sports Medicine, Inc., accessed Feb. 29, 2008 at <http://www.arthrotek.com/prodpage.cfm?c=0A05&p=090706> 2 pages.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Cayenne Medical; CrossFix® II System (product webpage); 4 pgs.; downloaded Nov. 21, 2011 (www.cayennemedical.com/products/crossfix/).

Depuy Mitek, Inc; Raynham, MA, "Versalok Surgical Technique for Rotator Cuff Repair: The next generation in rotator cuff repair," Product brochure, 2007 (month unavailble), 18 pages.

Linvatec Conmed Company, Largo, Florida, Product descriptions B17-19, B21; Tissue Repair Systems, Tissue Repair Accessories, and Master Arthroscopy Shoulder Instrument Set, (printed on or before Aug. 2007), 4 pages.

Ma et al; "Biomechanical Evaluation of Arthroscopic Rotator Cuff Stitches," J Bone Joint Surg Am, Jun. 2004; vol. 86(6):1211-1216.

Nho et al; "Biomechanical fixation in Arthroscopic Rotator Cuff Repair," Arthroscopy: J of Arthroscop and Related Surg; vol. 23. No. 1, Jan. 2007: pp. 94-102.

Schneeberger, et al; "Mechanical Strength of Arthroscopic Rotator Cuff Repair Techniques: An in Vitro Study," J Bone Joint Surg Am., Dec. 2002; 84:2152-2160.

Smith&Nephew; Fast-Fix Meniscal Repair System (product webpage); 4 pgs.; downloaded Nov. 21, 2011 (http://endo.smith-nephew.com/fr/node.asp?NodeId=3562).

Tornier, Inc.; CINCH(TM) Knotless Fixation Implant System; 510K (K080335); 6 pgs.; Feb. 6, 2008.

USS SportsMedicine ArthoSewTM Single Use Automated Suturing Device with 8.6 mm ArthroPort Cannula Set, Instructions for Use, <http:www.uss-sportsmed.com/imageServer.aspx? contentID=5020&contenttype=application/pdf> accessed Apr. 25, 2007, 2 pages.

Uss SportsMedicine ArthroSewTM Suturing Device, <http://www.uss-sportsmed.com/SportsMedicine/pageBuilder.aspx?webPageID=0&topicID=7141xsl=xsl/productPagePrint.xsl>, product description, accessed Apr. 25, 2007, 3 pages.

Saliman et al.; U.S. Appl. No. 13/247,892 entitled "Meniscus Repair," filed Sep. 28, 2011.

Saliman et al.; U.S. Appl. No. 13/323,391 entitled "Suture passer devices and methods," filed Dec. 12, 2011.

Saliman, Justin D.; U.S. Appl. No. 13/347,184 entitled "Implant and method for repair of the anterior cruciate ligament," filed Jan. 10, 2012.

Saliman et al.; U.S. Appl. No. 13/462,760 entitled "Methods of Meniscus Repair," filed May 2, 2012.
Covidien Surgical; Endo Stitch 10 mm Suturing Device; accessed Dec. 4, 2012 at <http://www.autosuture.com/autosuture/pagebuilder.aspx? topicID=7407&breadcrumbs=0:63659,30691:0,309:0> 2pages.
Medsfera; Suturing devices; accessed Dec. 4, 2012 at <http://www.medsfera.ru/shiv.html> 13 pages.
Asik et al.; Strength of different meniscus suturing techniques; Knee Sur, Sports Traumotol, Arthroscopy; vol. 5; No. 2; pp. 80-83; (month unavailable) 1997.

Asik et al.; Failure strength of repair devices versus meniscus suturing techniques; Knee Surg, Sports Traumatol, Arthrosc; vol. 10; No. 1; pp. 25-29; Jan. 2002.
Rimmer et al.; Failure Strength of Different Meniscal Suturing Techniques; Arthroscopy: The Journal of Arthroscopic and Related Surgery; vol. 11; No. 2; pp. 146-150; Apr. 1995.
Murillo et al.; U.S. Appl. No. 13/462,773 entitled "Suture Passer Devices and Methods," filed May 2, 2012.

* cited by examiner

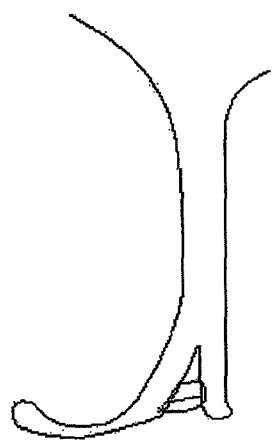
FIG. 1L
FIG. 1M

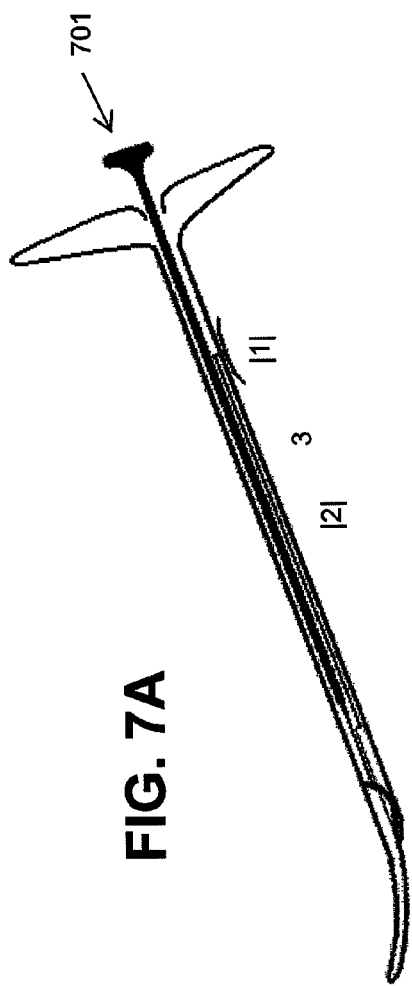
FIG. 7A
FIG. 7B
1st position
FIG. 7C
2nd position
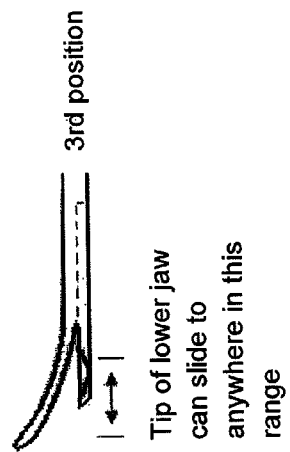
FIG. 7D
3rd position
Tip of lower jaw can slide to anywhere in this range

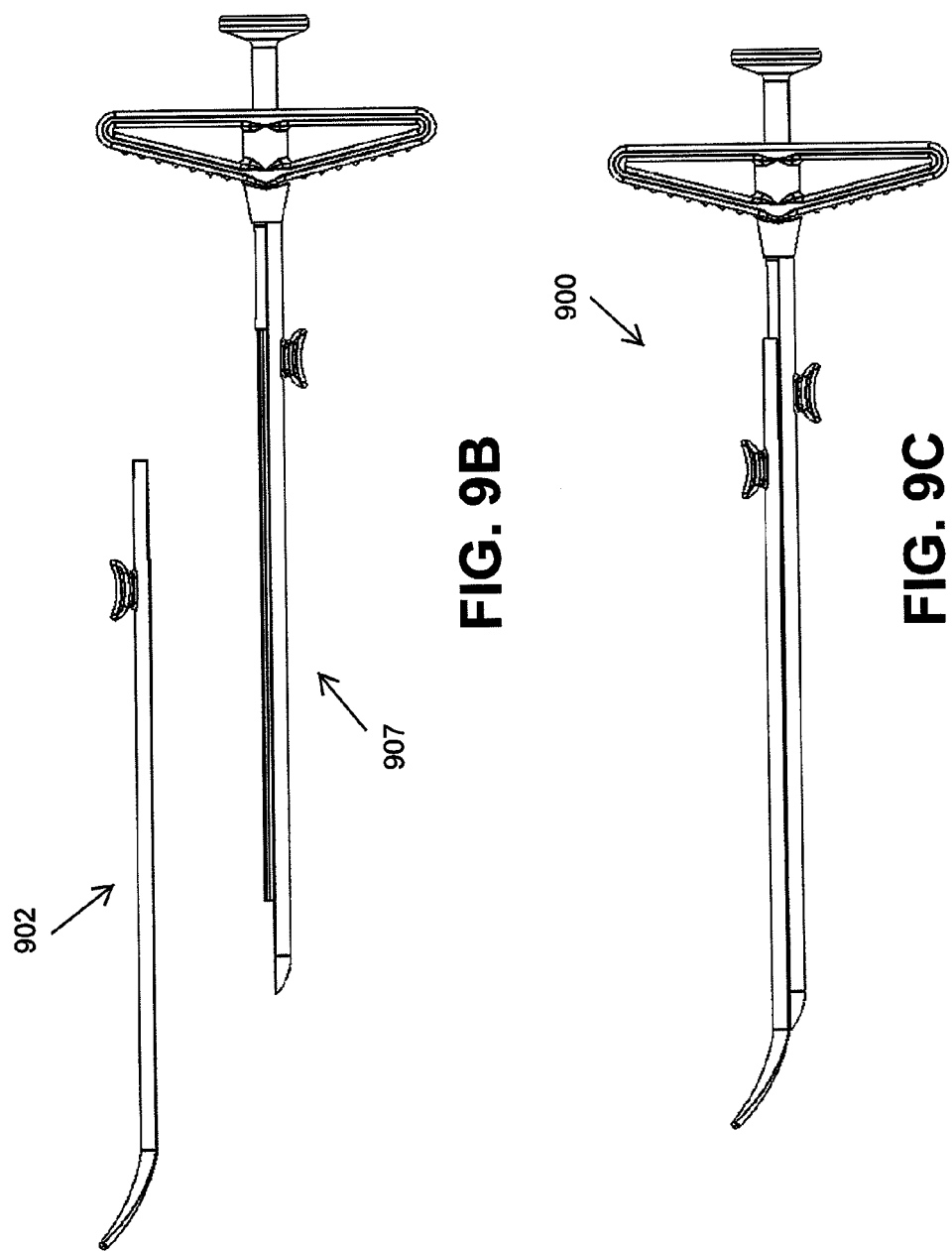

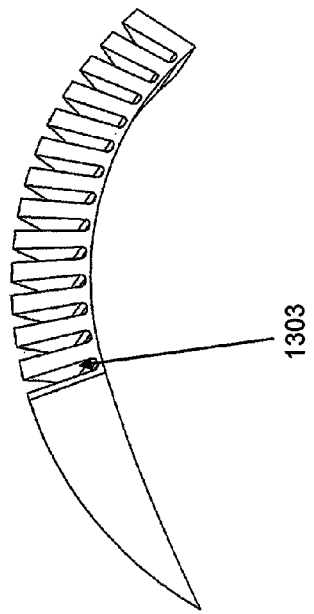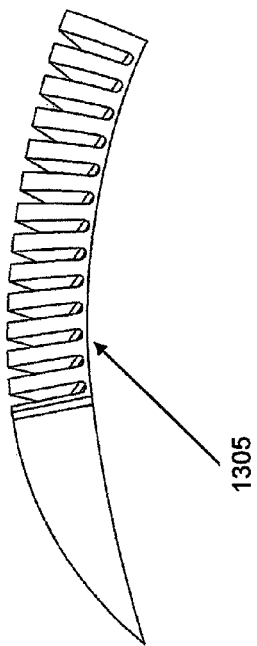
FIG. 13A
FIG. 13B

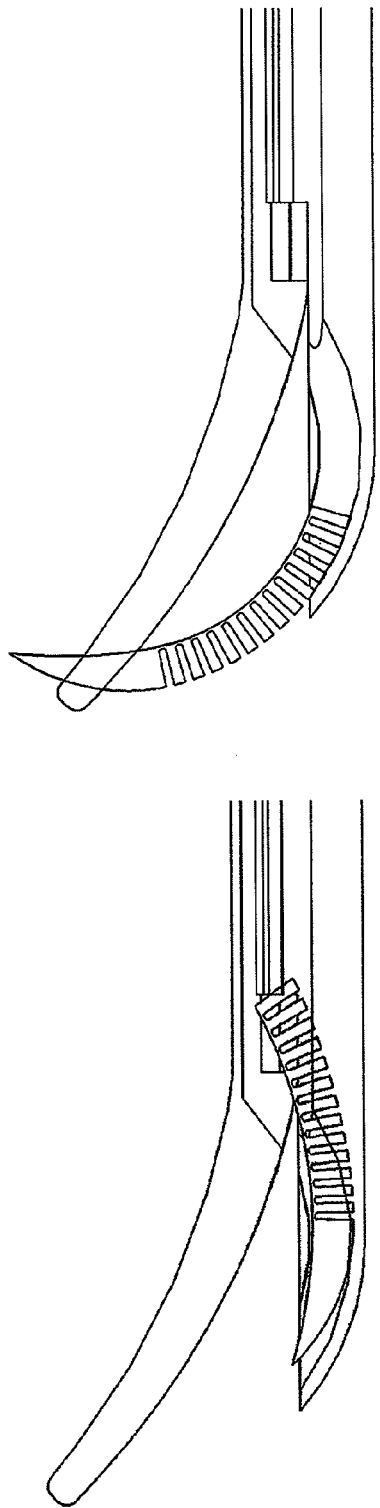
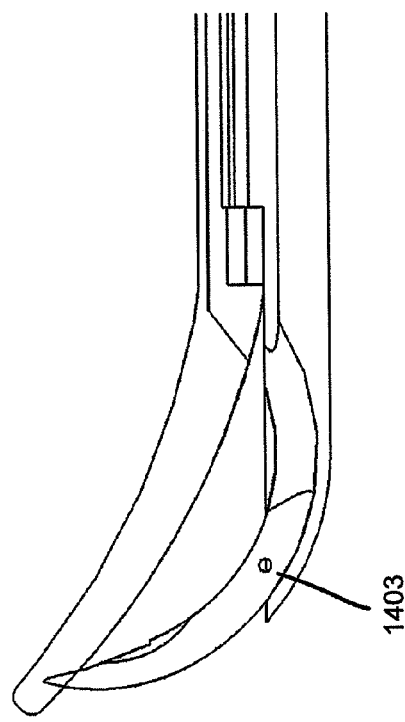
FIG. 14A
FIG. 14B
FIG. 14C

FIG. 15A
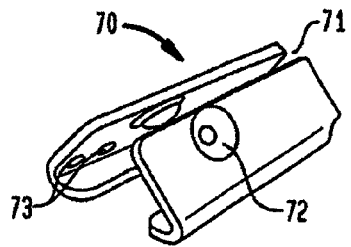
FIG. 15B
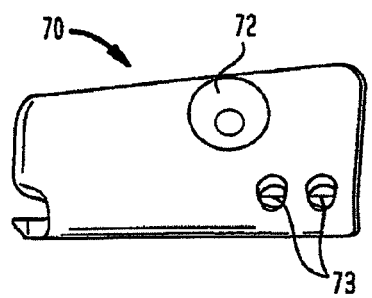
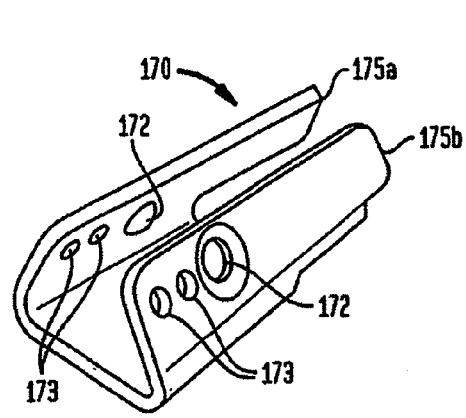
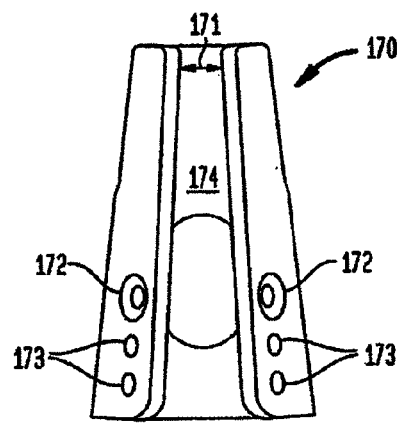
FIG. 16A
FIG. 16B
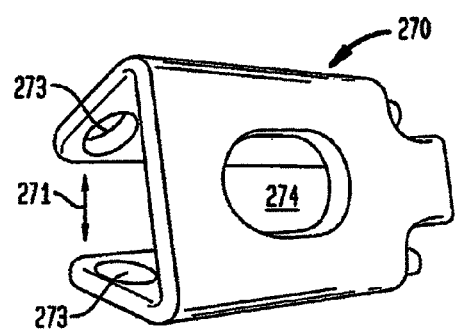
FIG. 17

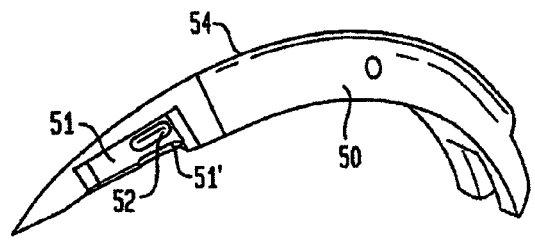
FIG. 18
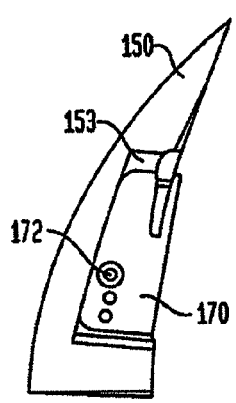 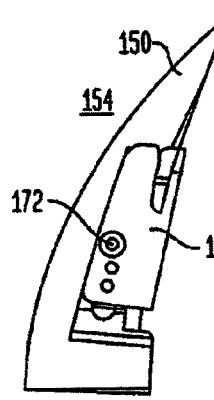 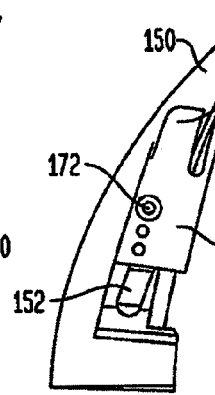 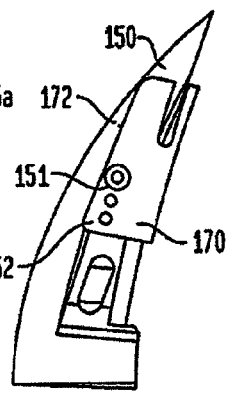
FIG. 19A   FIG. 19B   FIG. 19C   FIG. 19D
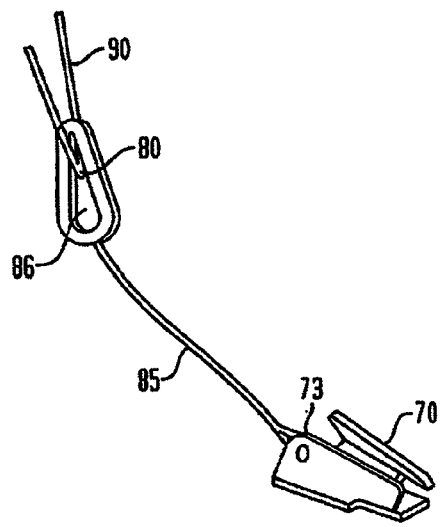
FIG. 20

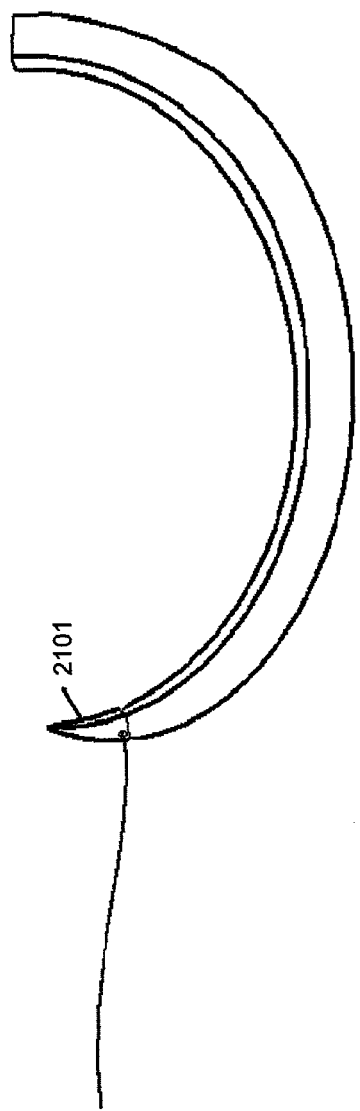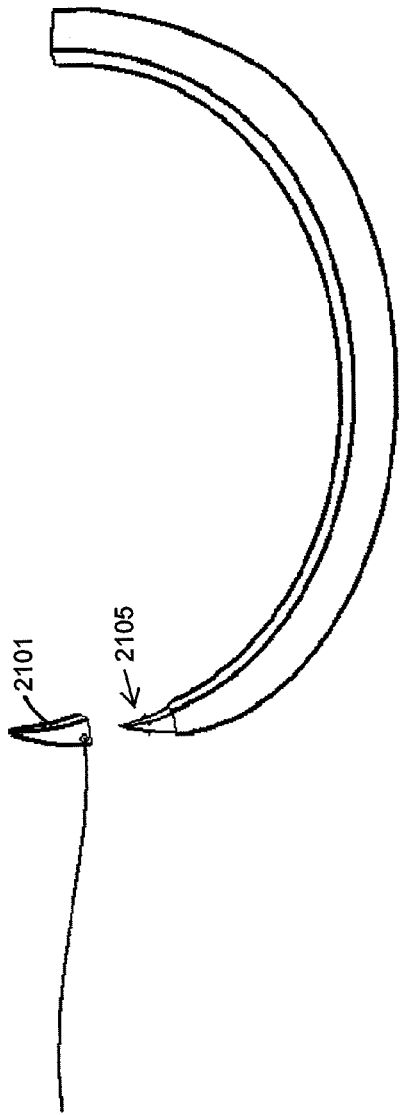

DEVICES, SYSTEMS AND METHODS FOR MENISCUS REPAIR

CROSS REFERENCE TO RELATED APPLICATIONS

This patent application is a continuation of U.S. patent application Ser. No. 12/942,803, titled "DEVICES, SYSTEMS AND METHODS FOR MENISCUS REPAIR," filed Nov. 9, 2010, now Publication No. US-2011-0112556-A1, which claims priority to U.S. Provisional Patent Applications: Ser. No. 61/259,572, titled "DEVICES, SYSTEMS AND METHODS FOR MENISCUS REPAIR," filed Nov. 9, 2009; Ser. No. 61/295,354, titled "DEVICES, SYSTEMS AND METHODS FOR MENISCUS REPAIR," filed Jan. 15, 2010; and Ser. No. 61/318,215 titled "CONTINUOUS SUTURE PASSERS HAVING TISSUE PENETRATING SUTURE SHUTTLES," filed Mar. 26, 2010. All of these applications are herein incorporated by reference in their entirety.

This application may also be related to U.S. patent application Ser. No. 11/773,388, titled "METHODS AND DEVICES FOR CONTINUOUS SUTURE PASSING," filed Jul. 3, 2007, now Publication No. US-2009-0012538-A1; and U.S. patent application Ser. No. 12/291,159, titled "SUTURE PASSING INSTRUMENT AND METHOD," filed Nov. 5, 2008, now Publication No. US-2010-0331863-A2. Both of these applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The devices, systems and methods described herein may be useful for the surgical repair of a torn meniscus. In particular, described herein are suture passers that are adapted for the effective and reliable passing of a suture to repair a torn meniscus.

BACKGROUND

The meniscus is a C-shaped piece of fibrocartilage which is located at the peripheral aspect of the joint (e.g., the knee). The central $2/3^{rds}$ of the meniscus has a limited blood supply while the peripheral $1/3^{rd}$ typically has an excellent blood supply. Young patients typically tear their menisci from traumatic events while degenerative tears are common in older patients as the menisci become increasingly brittle with age. Typically, when the meniscus is damaged, the torn piece begins to move in an abnormal fashion inside the joint, which may lead to pain and loss of function of the joint. Early arthritis can also occur due to these tears as abnormal mechanical movement of torn meniscal tissue and the loss of the shock absorbing properties of the meniscus commonly lead to destruction of the surrounding articular cartilage. Occasionally, it is possible to repair a torn meniscus. While this may be done arthroscopically, surgical repair using a suture may be difficult because of the difficult-to-reach nature of the procedure and the difficulty in placing sutures in a way to compresses and secures the torn surfaces.

Arthroscopy typically involves inserting a fiberoptic telescope that is about the size of a pencil into the joint through an incision that is approximately ⅛ inch long. Fluid may then be inserted into the joint to distend the joint and to allow for the visualization of the structures within that joint. Then, using miniature instruments which may be as small as 1/10 of an inch, the structures are examined and the surgery is performed.

FIGS. 2A-3 illustrate the anatomy of the meniscus in the context of a knee joint. As shown in FIG. 3 the capsule region (the outer edge region of the meniscus) is vascularized. A typical meniscus has a flattened ("bottom") and a concave top, and the outer cross-sectional shape is somewhat triangular. The outer edge of the meniscus transitions into the capsule. FIG. 4 illustrates the various fibers forming a meniscus. As illustrated in FIG. 4, there are circumferential fibers extending along the curved length of the meniscus, as well as radial fibers, and more randomly distributed mesh network fibers. Because of the relative orientations and structures of these fibers, and the predominance of circumferential fibers, it may be beneficial to repair the meniscus by suturing radially (vertically) rather than longitudinally (horizontally), depending on the type of repair being performed.

For example, FIGS. 5A-5E illustrate various tear patterns or injuries to a meniscus. Tears may be vertical/longitudinal (FIG. 5A), Oblique (FIG. 5B), Degenerative (FIG. 5C), including radially degenerative, Transverse or radial (FIG. 5D) and Horizontal (FIG. 5E). Most prior art devices for suturing or repairing the meniscus are only capable of reliably repairing vertical/longitudinal tears. Such devices are not typically recommended for repair of radial tears, particularly not arthroscopically/minimally invasively. FIGS. 6A-6C illustrate sutures placed with prior art devices to repair (via suturing) a torn meniscus (showing a longitudinal tear). FIG. 6A illustrates the results of a repair by a Smith&Nephew "Fast-T-Fix" device (comparable to a repair by a Biomet MaxFire device). FIG. 6B illustrates a Cayanne "CrossFix" device, and FIG. 6C illustrates a repair using an Arthrex meniscal "Viper" device.

In FIGS. 6A-6C the devices affecting these repairs require projection through the meniscus and substantially into the capsule region outside of the meniscus, which could potentially damage the nearby major nerves and large blood vessels. Further, the prior art devices, such as those placing the sutures illustrated in FIG. 6A-6C, typically place horizontal mattress suture patterns rather than vertical mattress suture patterns because vertical patterns are considerably more difficult for surgeons to place when using these devices. Vertical mattress patterns would have improved pull through strength because of the aforementioned predominance of circumferential collagen fibers found within the meniscus structure. Additionally, the devices forming the suture patterns illustrated in FIG. 6A-6C are only capable of point fixation; that is they cannot compress the tears uniformly across the torn surface. Finally, such prior art devices are designed for repairing peripheral vertical meniscus tears (torn from the superior surface to the inferior surface in line with the C-shape of the meniscus) and are incapable of repairing commonly encountered radial meniscus tears.

Thus, there is a need for methods, devices and systems for repairing a torn meniscus that are compatible with effective suturing. In particular, it would be beneficial to provide a device capable of suturing both radial and longitudinal tears. The methods, devices and systems described herein may address this need.

SUMMARY OF THE DISCLOSURE

Described herein are methods, devices and systems for repairing a torn meniscus. In particular, described herein are methods of repairing a meniscus that has a peripheral vertical meniscal tear or a peripheral radial meniscal tear that are compatible with arthroscopic (minimally invasive or semi-minimally invasive) techniques.

In general, the meniscus repair suture passer devices described herein are configured as continuous suture passers that may pass a suture back and forth between two arms or jaw between which the tissue (e.g., meniscus or adjacent tissues) is positioned. A meniscus repair suture passer may include a first arm (which may also be referred to as a lower arm) that is axially slideable relative to a second arm (which may also be referred to as an upper arm). The device may also include a tissue penetrator that extends between the arms, preferably in a curved or arcuate path. The tissue penetrator may alternately (cyclically) secure and release a suture (e.g., using a suture shuttle to which a suture may be connected), allowing the tissue penetrator to pull and push the suture shuttle between the first and second arm in cycles that alternate with leaving the suture shuttle (or, in some variations, the suture itself) in a dock, e.g., shuttle dock, on the arm that is opposite from the arm into which the tissue penetrator retracts into. These features may allow the meniscus repair suture passer to continuously pass a suture back and forth through a tissue without requiring that the suturing device be removed from the knee, or even removed off of the meniscus.

For example, described herein are meniscus repair suture passer devices that include: an elongate first arm extending distally and proximally along a long axis; an elongate second arm extending adjacent to the first arm along the long axis, wherein the first arm is axially movable distally and proximally relative to the second arm along the long axis, further wherein the distal end region of the second arm bends away from the long axis to form a distal opening between the second and first arms when the first arm is extended distally relative to the second arm; and a tissue penetrator configured to extend across the distal opening between the first and second arms to pass a suture therebetween. In some variations the second arm is also axially movable (e.g., relative to the rest of the device) along the long axis of the device. The suture may be connected to a suture shuttle, and thus the tissue penetrator may be configured to releasably connect to a suture shuttle that may be coupled to the suture.

The "arms" of the suture passer devices described herein may also be referred to as "jaws" or "members". Although in some variations the arms are elongate members, they may also be short members; the arms do not need to (although one or both of them may) extend the length (e.g., the length of the long axis) of the device. In some variations one or both arms may also be referred to as a shaft. For example, the second arm ("upper arm") may be referred to as an elongate shaft. In some variations the upper and lower arms may be included as part of an elongate shaft extending from the proximal to the distal end of the device.

The devices described herein may include a plurality of different axes, including a long axis. The long axis may be the longest axis of the device, or it may be long axis of the device not including the handle region, or some other sub-region of the device. For example, the long axis may define a proximal-to-distal axis of the device. The distal end of the device typically faces away from the handle, towards the patient, while the proximal end of the device typically faces a practitioner holding the device; the proximal end of the device may include a handle, while the distal end of the device engages tissue (e.g., the meniscus).

In general the first and second arms are axially movable (along the proximal-distal long axis) relative to each other, and/or relative to the rest of the device (e.g., a handle, an elongate housing or body region, etc.). In some variations the first arm is extendable or moveable along the long axis of the device relative to the second arm. The second arm may be fixed relative to the rest of the device, or it may also be axially movable relative to the long axis of the rest of the device. Conversely, the second arm may be axially movable or extendable relative to the first arm, which may be fixed (not movable) relative to the rest of the device or also axially movable or extendable. Axial motion may be referred to as sliding, pushing, pulling, or the like. This motion is typically in the proximal/distal direction, along the long axis. For reference, the motion of the tissue penetrator as described herein may (in some variations) be in an axis that is transverse to the long axis of the device.

A tissue penetrator is typically an elongate member that passes through the tissue and may push and/or pull a suture shuttle with it. Although in some variations the tissue penetrator may directly connect to a suture, in the principle embodiments described herein the tissue penetrator is configured for indirect coupling with a suture via a suture shuttle. This is described in greater detail below. A tissue penetrator may be solid or hollow, and may be curved, straight or bendable/curveable. In some variations the tissue penetrator has a sharp and/or pointed distal end. In some variations the tissue penetrator has one or more regions for engaging a suture or suture shuttle. For example, the tissue penetrator may include a clamping or anchoring region for releasably securing a suture shuttle.

In general, the first and second arms of the meniscus repair suture devices described herein may be positioned to form an opening (preferably an actute angled opening such as a v-shaped opening) when the first arm is extended relative to the second arm. This opening may be configured to correspond (or be slightly wider than) the angle of the superior surface and inferior (undersurface) of a meniscus. As mentioned, the meniscus are typically C-shaped fibrocartilaginous structures attached to the condylar surface of the tibia. The limbs of the C face centrally. The superior meniscal surface is generally concave, which enhances contact with the curvilinear-shaped femoral condyle. Conversely, the undersurface of the meniscus is generally flat, which enhances contact with the flattened tibial plateau. The periphery (outer portion) of the meniscus is thicker than the pointed central portion. The thick periphery allows for a firm attachment to the joint capsule. Thus, in general, the first and second arms of the devices described herein may be configured to fit this generic anatomy (and may be sized to fit specific anatomies or ranges of anatomies). For example, the first arm may be straight and configured to fit beneath the flat undersurface of the meniscus, while the second arm forms a bend with the first arm approximating the angle between the superior surface and undersurface of the meniscus (e.g., the maximum angle, or an average of the angle of this somewhat convex surface).

For example, the distal opening of the devices formed between the first and second arms may be an acute-angled distal facing opening configured to fit the meniscus therein. The distal opening may be a v-shaped distal opening between the second and first arms when the first arm is extended distally relative to the second arm, configured to receive a meniscus.

In general, when the first arm, which is typically "straight" or extending in the same direction as the long axis of the device, is retracted proximally, the lower "arm" of the distal opening is missing, so the device has just a narrow, bent, distal end formed by the distal end region of the second arm. This distal end region may be used to position the device within the knee near the meniscus. The small size and dimensions of the distal end when the first arm is retracted proximally (completely) may allow the device to navigate the tissue of the knee without undue damage to other tissues. Extending the first (lower) arm distally may form the "v-shape" mentioned above. In general, the tips of the distal ends of the second and first arms are rounded and atraumatic. In particular, the tips may be blunt to prevent damage to tissue as the device is positioned.

In some variations, the tissue penetrator is configured to be housed within the distal end of the first arm. The tissue penetrator may be completely retracted into the first arm, which may prevent damage to tissue as the device is maneuvered into position around the meniscus. In some variations, the tissue penetrator is configured to extend from the second, rather than the first arm, in which case the configuration of the tissue penetrator and dock (e.g., shuttle dock) may be reversed.

The meniscus repair suture devices described herein may also include a proximal handle having a first control for axially moving at least the distal end region of the first arm relative to the second arm. A proximal handle may be configured for gripping (in a single hand or using both hands), and may have a tissue penetrator control for controlling the extension and retraction of the tissue penetrator across the distal opening formed by the second arm and the extended first arm.

As mentioned, a meniscus repair suture device may also include a dock at the distal end region of the second arm configured to alternately release and retain the suture, permitting the tissue penetrator to pass the suture from the first arm to the second arm and back to the first arm. In some variations, this dock is a shuttle dock that is configured to releasably secure a suture shuttle (to which a suture may be directly or indirectly connected) for exchange between the tissue penetrator (which may ferry the shuttle dock and any connected suture) back and forth between the first and second arms, alternately leaving the suture shuttle in the shuttle dock on the arm opposite from the arm to which the tissue penetrator is attached and housed.

Thus, in some variations the meniscus repair suture device also includes a shuttle dock at the distal end region of the second arm configured to alternately release and retain the suture shuttle, permitting the tissue penetrator to pass the suture shuttle from the first arm to the second arm and back to the first arm. In variations in which the tissue penetrator extends and retracts into the second arm, the first arm may include a shuttle dock. In some variations the devices include a plurality of shuttle docks, e.g., at the distal end region of the second arm, that are each configured to alternately release and retain the suture shuttle, permitting the tissue penetrator to pass the suture shuttle from the first arm to the second arm and back to the first arm.

The tissue penetrator may be configured to extend across the distal opening in a curved path. For example, the tissue penetrator may be curved or curveable (e.g., via a hinged region, shape-memory material, etc.). In general, the tissue penetrator may include a clip region to which a suture shuttle may releasably secure.

Any of the devices described herein may be configured for re-use. For example, in some variations a portion of the device is "durable" (re-usable) and a portion of the device is disposable. For example, in some variations the second arm is configured to be detachable from the device, and disposed of. In some variations the second arm includes a suture shuttle and/or an attached suture that is pre-loaded into the second arm (or shaft). Thus, in some variations, the second arm is configured to be disposable and to detachably connect to a reusable first arm. The first arm may be extended or retracted axially as mentioned above. In general, the first arm may include a final stop that limits or prevents the movement of the first arm distally along the long axis of the device by preventing the first arm from extending beyond this stop. For example, the final stop may prevent the distal tip of the first arm from extending beyond a position on the device in which the tip of the first arm and the tip of the second arm form a right angle relative to the long axis of the device, which may be the same as the long axis of the first arm.

In some variations, the devices described herein include a plurality of "stops" that indicate to a user the axial position of the first arm along the distal to proximal long axis of the device. These stops, unlike the final stop, may not prevent axial movement of the first arm relative to the device, but they may indicate positions in which the first arm of the device may be held static by some manner, or where a slight increase in resistance to axial motion may be felt. These positions may correspond to known positions of the first arm relative to the upper arm (e.g., fully withdrawn, extended halfway across the device, fully extended, or intermediate positions between these). In some variations these stop positions may correspond to positions in which the tissue penetrator, if extended while the first arm is at this stop position, will engage a shuttle dock.

Any of the devices and components described herein may be included as part of a kit. For example, described herein are kits comprising a meniscus repair suture passer and a suture shuttle. In some variations the kit includes a suture. In some variations the kit may include a removable (or multiple removable) second arm or shaft region. This second arm may include one or more shuttle docks pre-loaded with a suture shuttle and/or suture.

Also described herein are meniscus repair suture passer device for passing a suture through the meniscus, the device comprising: an elongate shaft extending distally and proximally along a long axis; a first arm that is movable distally and proximally relative to the long axis; wherein the shaft comprises an second distal end region that bends away from the long axis of the shaft to form a v-shaped distal opening with the first arm when the first arm is extended distally; a tissue penetrator configured to extend across the distal opening between the second and first arms in a curved pathway and to pass a suture shuttle therebetween; and a shuttle dock having an opening configured to alternately release the suture shuttle onto the tissue penetrator and to receive and hold the suture shuttle from the tissue penetrator.

As mentioned, the shuttle dock may comprise a releasable lock configured to alternately release the suture shuttle onto the tissue penetrator and to receive and hold the suture shuttle from the tissue penetrator. The shuttle dock may be on the second distal end region of the shaft.

Also described herein are meniscus repair suture passer devices for continuously suturing tissue to repair a torn meniscus, including: an elongate first arm extending distally and proximally along a long axis, wherein at least the distal end of the first arm is axially movable distally and proximally relative to the long axis; an elongate second arm extending along the long axis, wherein the distal end region of the second arm bends away from the long axis to form a v-shaped distal opening with the first arm when the first arm is extended distally; a tissue penetrator housed within the distal end region of the first arm, the tissue penetrator configured to extend across the distal opening between the second and first arms and pass a suture shuttle therebetween; and a shuttle dock at the distal end region of the second arm configured to alternately release the suture shuttle onto the tissue penetrator and to receive and hold the suture shuttle from the tissue penetrator, permitting the tissue penetrator to pass the suture shuttle from the first arm to the second arm and back to the first arm.

Although many of the examples described herein describe meniscus repair suture devices that are configured to indirectly couple with a suture using a suture shuttle, in some variations the device may be configured to pass a suture back and forth through tissue without requiring a shuttle. For example, in some variations, the tissue penetrator is configured to releasably connect to a suture, to pull the suture across the tissue a first time (e.g., from the second arm to the first arm) and then, after repositioning the device relative to the meniscus, pushing the suture across the tissue again (e.g., from the first arm to the second arm), where the suture may be released from the tissue penetrator into a dock that retains the suture at the second arm.

Methods of repairing the meniscus using any of the meniscus repair suture passer devices described herein are also described. For example, described herein are methods of repairing a torn meniscus using a continuous suture passer having a first arm and a second arm and a distal to proximal long axis, the method comprising: placing the distal end region of the second arm of the suture passer adjacent to one side of the meniscus, wherein the distal end region of the second arm is bent relative to the long axis of the suture passer; extending the distal end region of the first arm of a suture passer distally relative to the long axis of the suture passer, wherein the first arm extends under an opposite side of the meniscus so that the distal end regions of the first and second arms of the suture passer form a v-shaped opening in which at least a portion of the meniscus is positioned; extending and withdrawing a tissue penetrator across the opening between the first and second arms to pass a suture between the first and second arms; repositioning the suture passer without removing the suture passer from the meniscus; and extending and withdrawing the tissue penetrator across the opening between the first and second arms to pass the suture between the first and second arms a second time.

In some variations, the step of placing the distal end region of the second arm comprises placing the distal end region of the second arm adjacent to the superior side of the meniscus. The second arm may be used to help position the first arm, using the tip of the second arm to cause the central aspect of the meniscus to flip upward a few degrees, allowing easier access for the first arm to slide under the meniscus (the inferior or undersurface of the meniscus). For example, the step of placing the distal end region of the second arm may include applying outward pressure on the capsule just superior to the peripheral meniscus tissue.

The step of extending the distal end region of the first arm may include sliding the first arm distally relative to the long axis to position the tip of the distal end region of the first arm beneath the undersurface of the meniscus opposite from the superior surface.

The step of extending the distal end region of the first arm may comprises sliding the first arm distally relative to the long axis to a fully extended position. The step of extending the distal end region of the first arm may include sliding the first arm distally relative to the long axis comprises extending the distal end region until a stop is reached.

In general, the steps of extending and withdrawing the tissue penetrator comprise extending and withdrawing the tissue penetrator along a curved path between the first and second arms. The step of extending and withdrawing a tissue penetrator across the opening between the first and second arms to pass a suture between the first and second arms may comprise extending the tissue penetrator from within the first arm, through tissue, and engaging a shuttle dock within the second arm before withdrawing the tissue penetrator back into the first arm. In some variations, the step of extending and withdrawing a tissue penetrator across the opening between the first and second arms to pass a suture between the first and second arms comprises extending the tissue penetrator from within the first arm, through tissue, and engaging a suture shuttle held within the second arm, and withdrawing the suture shuttle secured to the tissue penetrator back into the first arm.

During use, the suture passer may be repositioned relative to the meniscus either by moving the entire suture passer, or by moving a portion of it (e.g., the first arm) so that the device may place a second stitch thought the tissue in a different location than the first stitch. For example, the step of repositioning the suture passer may include moving the first arm proximally relative to the long axis of the device. In some variations, the step of repositioning the suture passer comprises moving the first arm proximally relative to the long axis of the device to an intermediate stop. The step of repositioning the suture passer may comprise moving the first arm distally relative to the long axis of the device. In some variations, the step of repositioning the suture passer comprises moving suture passer longitudinally relative to the meniscus.

The second round of extending and withdrawing the tissue penetrator may be used to pass an additional stitch through the tissue. For example, the step of extending and withdrawing the tissue penetrator across the opening between the first and second arms to pass a suture between the first and second arms a second time may comprise extending the tissue penetrator having a suture shuttle attached thereto from within the first arm, through tissue, and engaging a shuttle dock within the second arm, and withdrawing the tissue penetrator back into the first arm while leaving a suture shuttle in the shuttle dock.

In any of the methods described herein, the methods may include repeating the steps of repositioning and extending and withdrawing the tissue penetrator across the opening between the first and second arms to pass the suture between the first and second arms multiple times.

Also described herein are methods of teaching repair of torn meniscus. Methods of teaching repair of a torn meniscus may include teaching any of the methods for repairing a torn meniscus described herein. Teaching may include providing written instructions, oral instructions, visual instructions, audio/visual instructions, or the like. Instructions may be provided in electronic or non-electronic formats.

Also described herein are method of repairing a torn meniscus using a continuous suture passer having a first arm and a second arm and a distal to proximal long axis, the method comprising: placing the distal end region of the second arm of the suture passer adjacent to the superior side of the meniscus, wherein the distal end region of the second arm is bent relative to the long axis of the suture passer; extending the distal end region of the first arm of a suture passer distally relative to the long axis of the suture passer, to position the first arm under the side of the meniscus opposite the superior surface, so that the distal end regions of the first and second arms of the suture passer form a v-shaped opening in which at least a portion of the meniscus is positioned; extending a tissue penetrator from the first arm, in a curved path through tissue across the opening between the first and second arms to engage a suture shuttle held by a shuttle dock on the second arm; withdrawing the tissue penetrator back into the first arm while drawing the suture shuttle through the tissue; repositioning the suture passer without removing the suture passer from the meniscus; extending the tissue penetrator with the suture shuttle from the first arm, in a curved path through tissue across the opening between the first and second arms to engage a suture shuttle held by a shuttle dock on the second arm; and withdrawing the tissue penetrator back into the first arm while leaving the suture shuttle in the shuttle dock on the second arm. In some variations, these methods may also include repeating the steps of repositioning the suture passer, extending the tissue penetrator from the first arm, in a curved path through tissue across the opening between the first and second arms to engage the suture shuttle held by the shuttle dock, and withdrawing the tissue penetrator back into the first arm while drawing the suture shuttle through the tissue.

BRIEF DESCRIPTION OF THE DRAWINGS

FIGS. 1I-1M illustrate removal of the suture passer, retaining the suture in position.

FIG. 7A shows one variation of a meniscus repair suture passer as described herein.

FIGS. 7B-7D illustrate various preset (e.g., 'lock') positions for the meniscus repair suture passer shown in FIG. 7A.

FIGS. 9B and 9C show another variation of a meniscus repair suture passer.

FIGS. 13A and 13B show one variation of a curved tissue penetrator in a relaxed and curved (FIG. 13A) and a straightened (FIG. 13B) configuration.

FIGS. 14A and 14B illustrate the curved tissue penetrator of FIGS. 13A and 13B retracted into the lower arm/jaw (FIG. 14A) and extending from the lower arm/jaw (FIG. 14B) to pass a suture shuttle from the lower to the upper arm/jaw.

FIG. 14C illustrates another variation of a curved or curvable tissue penetrator.

FIGS. 15A and 15B illustrate one embodiment of a suture shuttle.

FIGS. 16A and 16B illustrate another embodiment of the suture shuttle.

FIG. 17 illustrates yet another embodiment of the suture shuttle.

FIG. 18 illustrates one embodiment of a tissue penetrator.

FIGS. 19A-19D illustrate one embodiment of the interaction between the suture shuttle and the tissue penetrator.

FIG. 20 illustrates a first embodiment of a suture clip.

FIG. 21A shows one variation of a tissue-penetrating suture shuttle (with a connected suture) connected/coupled to a tissue penetrating element.

FIG. 21B shows the tissue penetrating suture shuttle of FIG. 21A separated from the tissue penetrating element.

FIG. 22B shows the distal tissue penetrating suture shuttle separated from the tissue penetrating element of the device.

DETAILED DESCRIPTION

Figure 1A:
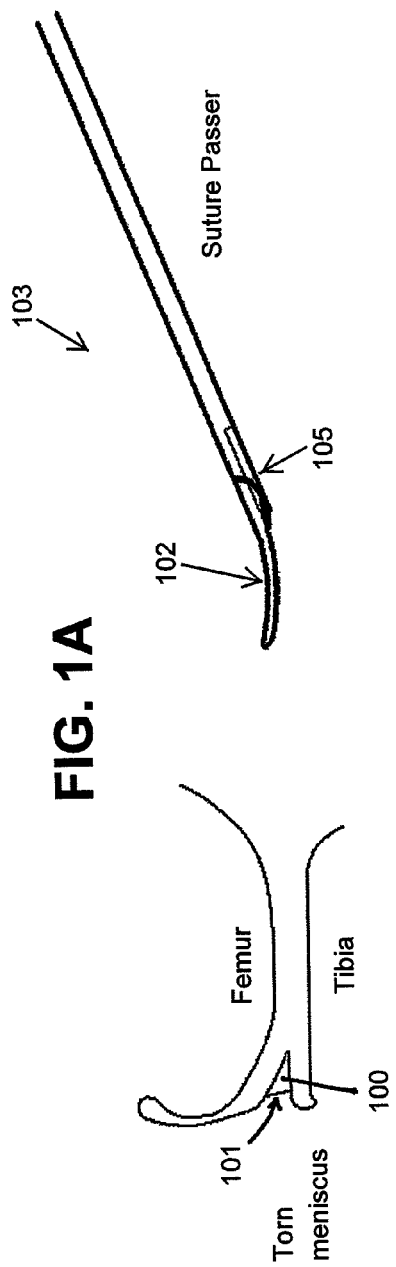
FIG. 1A shows a schematic of a portion of a torn meniscus between a femur and tibia and a suture passer to the right.

Described herein are suture passers for meniscus repair. In general, these devices may be referred to herein as meniscus repair suture passers, meniscus repair devices, or simply suture passers. The devices described herein may be configured to repair a meniscus (knee joint meniscus), and may have two arms which extend longitudinally and can be expanded around a meniscus from a lateral (central) approach. Typically, the distal end region (e.g., the distal-most 3 or less cm) of one of the arms is bent or bendable at an angle away from the long axis of the device, and the other arm is axially movable distally and proximally (in the direction of the long axis of the device). Extending the distally and proximally movable arm distally will form an acute angled opening at the distal end that can be positioned around the meniscus, and a suture can be passed from one arm to the other through the meniscus or adjacent tissues to repair meniscal tears. The suture may be passed back and forth through the tissue multiple times by using a tissue penetrator that can extend and retract from just one of the arms to move a suture shuttle between the two arms.

Thus, the meniscus repair suture passer devices described herein may pass a suture two or more times through the meniscus so that the suture passes over the top and bottom of the meniscus. The angle and/or position of the device may be adjusted as necessary before and during the procedure, including between passing the suture through various portions of the meniscus. Thus, the meniscus repair suture passers describe herein are adapted for percutaneous use.

In general, a system including a suture passer as described herein may include a first arm, a second arm, a suture-passing tissue penetrating element (e.g., needle), a shuttle for passing a suture, and one or more shuttle seats for releaseably retaining and releasing the suture shuttle. In some variations the tissue penetrating element is a curved needle element that is configured to extend from the first or second arm (from which it may be extended and retracted), through tissue (or air), and approach the second or first arm, where it may engage or disengage (alternately or cyclically) a suture shuttle held in a shuttle seat. In some variations, the first arm of the suture passer may be configured for axial movement (e.g., forward and backwards along the long axis of the device). The suture passer may be configured so that the first arm includes two or more stops. For example, the first arm may include a first stop in which the first arm is fully retracted axially, so that the first arm is retraced proximally while the second arm extends distally, and a second stop (extended stop) when the first arm is fully extended distally so that the tissue penetrating element (e.g., needle) may be extended from the first arm to engage a shuttle seat on the second arm. In some variations the suture passer includes a third or more (e.g., intermediate) stop(s) in which the first arm is partially extended distally at a position where the tissue penetrating element may be extended from the first arm to engage a second shuttle seat on the second arm. This is illustrated in FIGS. 7B-7D, described below.

One or more arms of the suture passer may be bent or curved. For example, the second arm of the device may be bent, curved, or angled (e.g., "upwards" away from the first arm, or from the long axis of the device, including the first arm) so that the ends region of the second arm (the upper arm) relative to the long axis is bent at approximately the angle of the meniscus (e.g., the superior face of the meniscus). The angle may be fixed (e.g., at an acute angle of approximately 10°, 15°, 20°, 25°, 25°, 30°, 35°, 40°, 45°, 60°, etc. including any angle between 1° and 90°). For example, the angle may be between 20 degrees and 50 degrees. In some variations, the angle between the first and second arms is variable (e.g., either or both arms may be bent or adjusted to adjust the angle therebetween). The angle of the bend in the upper (second) arm may be approximately the average angle between the superior and inferior faces of the meniscus; for example, the angle may be approximately 35 degrees+/−2 degrees, 5 degrees, 7 degrees, 10 degrees, 15 degrees, etc. In general the bend forms an acute angle with the lower (second) arm when the second arm is extended distally. In some variations, as mentioned, the distal end region of the second arm may be bendable from a straight or pre-bent configuration into the final bend configuration.

As mentioned, the second arm may include one or more shuttle seats. In general, the shuttle seats may be configured to releaseably engage a suture shuttle to which the suture can be connected. The suture shuttle is thereby passed between the shuttle seat on the second arm and the tissue penetrating element that may extend and retract into the first arm. The suture shuttle and tissue penetrating element may be configured as described in the descriptions previously incorporated by reference (e.g., U.S. Ser. No. 11/773,388 and U.S. Ser. No. 12/291,159). For example, the shuttle may be a clip (e.g., a triangular-shaped clip) to which a suture is secured; the clip may be configured to snap on an off of the tissue penetrating element (e.g., a curved needle having a triangular cross-section). In some variations, the suture shuttle with a suture attached is pre-loaded into the distal-most shuttle seat on the first arm of the device. FIGS. 15A-22B, described in more detail below, illustrate some variations of suture shuttles and attachment regions to various tissue penetrators.

A tissue penetrating element may be a curved member that retracts or extends from one of the arms. In particular, a tissue penetrating member may be a curved or curvable element that retracts completely into a housing in the distal end region of the first arm, and extends outwards in a curved pathway. In some variations, the tissue penetrator may be configured to extend from the distal end region of the second arm, and to retract fully into the body of the second arm; in some variations a portion of the tissue penetrating member may extend from the first arm even when fully retracted into the first arm. The second arm or other portions of the suture passer may be configured to include a track or pathway for the tissue penetrating member so that the tissue penetrating member does not prevent the first arm from extending or retracting axially relative to the body of the device.

FIGS. 1A-1M show one variation of a suture passer used to repair a torn meniscus. These figures illustrate the operation of the device to repair a peripheral vertical tear in a meniscus.

For example, FIG. 1A shows a sagittal cross-section through a patient's knee. A portion of the meniscus is shown. The vertical tear 101 (shown as a line) in the peripheral region of the meniscus 100 is illustrated. The femur is shown above the tibia, with the torn edge of the meniscus between the two. One variation of a continuous suture passer 103 is shown to the right of the cross-section through the knee. The suture passer may be inserted into the joint via an arthroscopic or an open (or semi-open) surgical procedure. For example, in some variations the torn meniscus may be accessed and visualized arthroscopically; the suture passer may be inserted through a separate incision or through the same incision.

Figure 1B:
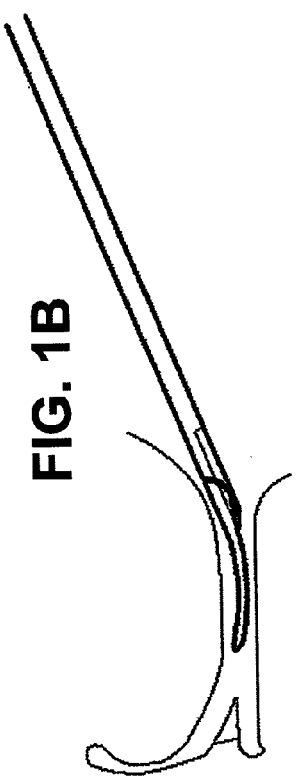
FIGS. 1B-1D illustrate insertion of the suture passer surgical device into the joint and around the torn meniscus.
Figure 1C:
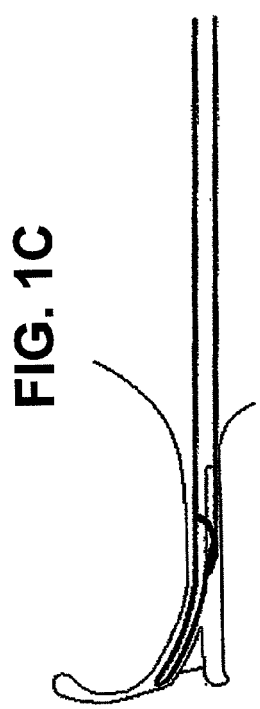

In this example, the suture passer is inserted in a collapsed or retracted configuration, in which the first arm 105 is retracted proximally (e.g., towards a handle or control at the proximal end). The second arm 107 extends from the distal end (and may be fixed in this extended position, or it may be adjustable or extendable). The second arm 107 shown in this configuration is curved ('upwards') so that it can be inserted around the torn meniscus, as shown in FIGS. 1B-1C. The entire suture passer is sized for use in this space. For example, the suture passer may have a diameter in the un-extended/delivery configuration that is less than a typical (or size-appropriate) space between the femur and tibia, i.e., less than about 10 mm, less than about 9 mm, less than about 8 mm, less than about 7 mm, less than about 6 mm, etc. This diameter may include the diameter of the first arm, which may have an individual diameter of less than about 5 mm, less than about 4 mm, less than about 3 mm, less than about 2 mm, etc.

Figure 1D:
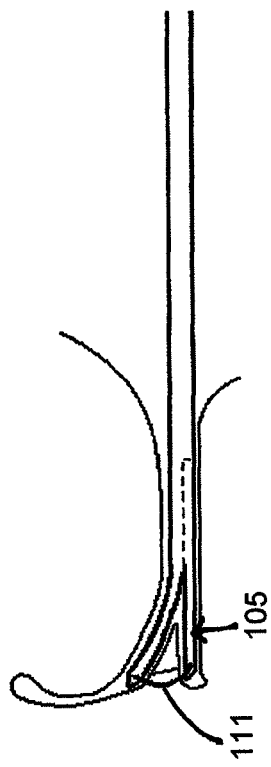

The distal end of the suture passer, formed by the distal end region of the second arm, may thus be extended into the tissue and above the torn meniscus, as illustrated in FIGS. 1A-1C. Once the second (upper) arm is positioned, the first (lower) arm 105 may be extended from the device, as illustrated in FIG. 1D. In this example, the first arm is extended from the proximal region of the device, so that it may extend under the meniscus, opposite from the second arm. The first arm may be straight (as shown in FIGS. 1A-1K), or it may be curved or bendable.

In the illustrated method of FIGS. 1A-1K, the first, lower, arm is extendable axially from the body of the device. The lower arm extends forward by sliding underneath the inferior surface of the meniscus and towards the capsule of the underside of the meniscus. The lower arm may be extended to the most distal "stop." The distal stop may be indicated by a resistance (e.g. a physical stop), and may be locking. For example, the second arm may click into position when held in a stop on the suture passer. A handle or control on the device may be used to disengage and withdraw the device.

Figure 1E:
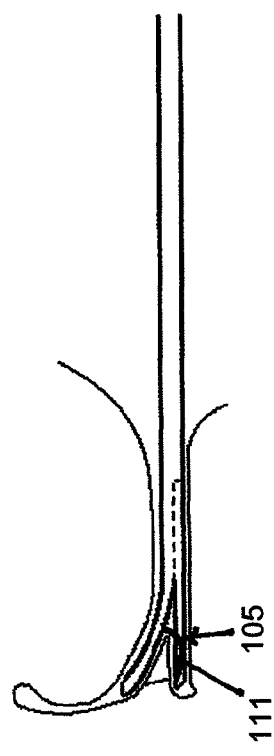
FIGS. 1E-1H illustrate passing the suture through the meniscus multiple times using the suture passer as described herein.
Figure 1F:
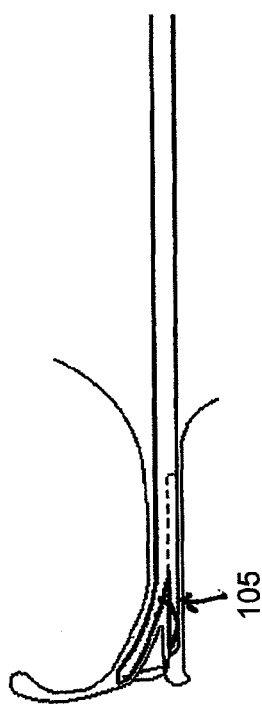

Once the first arm is in the desired axial position (e.g., fully extended or otherwise) relative to the first arm, the suture may be passed. For example, FIG. 1E illustrates the initial step of extending the tissue penetrating element (needle) 111 from within the first arm and across the space separating the first and second arms. In this variation, the tissue penetrating element is a curved needle that is pushed from the distal end region of the device as illustrated to pass through the meniscus as shown. Initially, the tissue penetrating member just forms a pathway through the tissue; the shuttle and suture are held within the second arm. In this example, the needle penetrates through the peripheral menisocapsular tissue and mates with a complementary region of the second arm, the first distal shuttle seat. The shuttle and an attached suture are initially pre-loaded into the distal shuttle seat. Contacting the shuttle seat with the tissue penetrating member when the shuttle is already held in the shuttle seat may cause the shuttle to snap onto tissue penetrating member, and release the shuttle from the seat, as illustrated in FIG. 1E. Thereafter, the shuttle and any attached suture 113 may be withdrawn back through the meniscus on the tissue penetrating member as it is retracted into the second arm, as illustrated in FIG. 1F. The suture is thereby drawn across and through the meniscus.

In some variations the device is configured so that the tissue penetrating element (e.g., needle, etc.) may be extended only when the lower arm is extended to a position from which the tissue penetrating element may mate with the receiving site (e.g., shuttle seat) on the opposite arm.

Figure 1G:
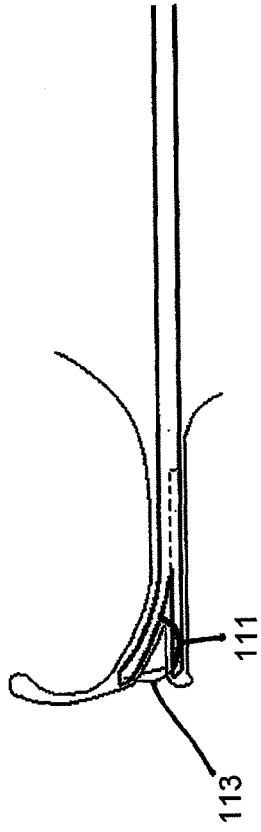
Figure 1H:
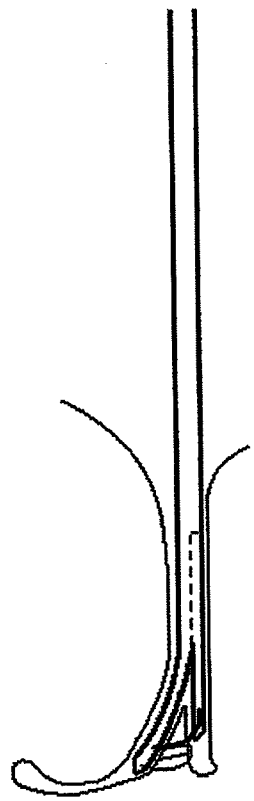

In FIG. 1G, the first (lower) arm 105 can then be retracted slightly. In any of these variations, the arms may be referred to as forming a "jaw" and thus the second arm may be referred to as the upper or second jaw and the first arm may be referred to as the first or lower jaw. In this example, the first arm is retracted into a stop position that is located proximal to the distal end. This second stop may be referred to as the intermediate or second stop position (the distal end position is the first or distal stop, and the fully retracted position may be referred to as the proximal stop position). The device may hold or releasably "lock" the first arm in this position so that the tissue penetrating member (to which the shuttle is now attached) may be extended back through the meniscus, in a region located more peripheral to the tear, as illustrated in FIGS. 1G and 1H. Meanwhile, the upper (second) arm is left securely in place. In some variation (e.g., anatomy permitting), the second arm may also be slightly withdrawn proximally, or the entire device may be moved laterally or proximally to position an additional stitch at a different position.

In some of the variations described herein, the lower arm (e.g., the arm including the tissue penetrating element) may be longitudinally extended/retracted relative to the rest of the device. In some variations the upper arm may be extended/retracted relative to the rest of the device. This is illustrated below in the variations shown in FIGS. 9-10B.

Figure 1I:
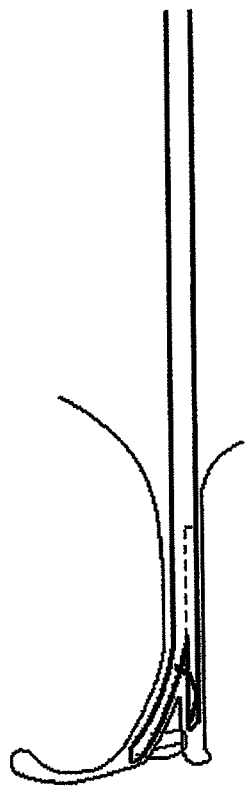

Returning now to FIG. 1H, the tissue penetrating member with attached shuttle and suture is again extended, this time penetrating on the opposite side of the tear from the previous stitch, so that the tear may be stitched closed. The needle is passed until it engages (distally) with a second shuttle seat region of the second arm; when this occurs the shuttle is held securing in the shuttle seat and is uncoupled (e.g., unclipped, or removed) from the tissue penetrating element, so that the tissue penetrating element can be withdrawn to leave the shuttle behind in the shuttle seat on the second arm, as illustrated in FIG. 1I. In some variations the suture passer may be moved slightly (e.g., laterally out of the plane of the cross-section shown) to again pass the suture by repeating some of the steps above, e.g., from FIG. 1E forwards, or it may be removed.

Figure 1J:
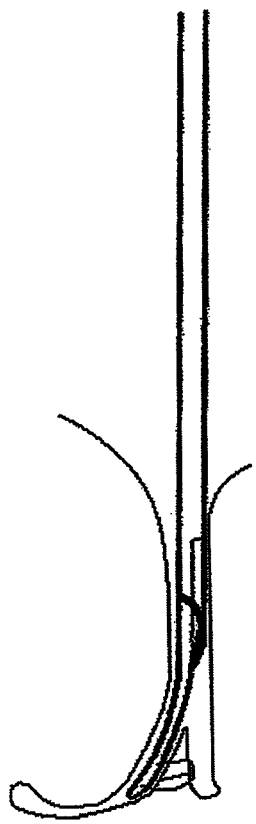
Figure 1K:
Figure 2B:
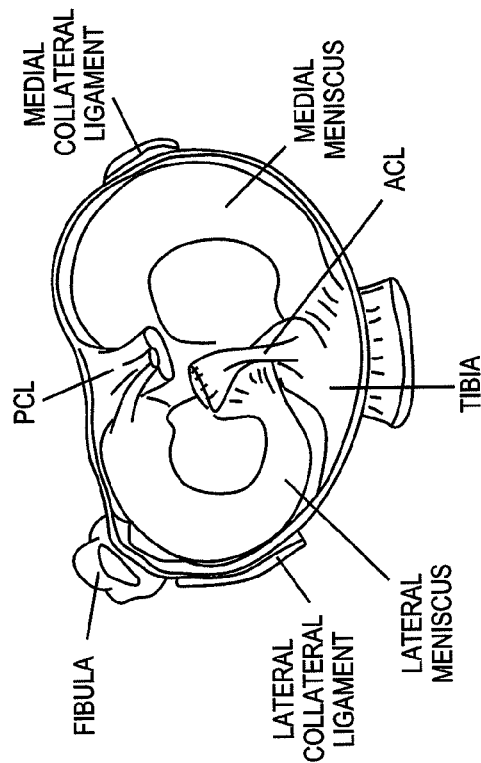
FIGS. 2A and 2B illustrate the anatomy of the meniscus.
Figure 2A:
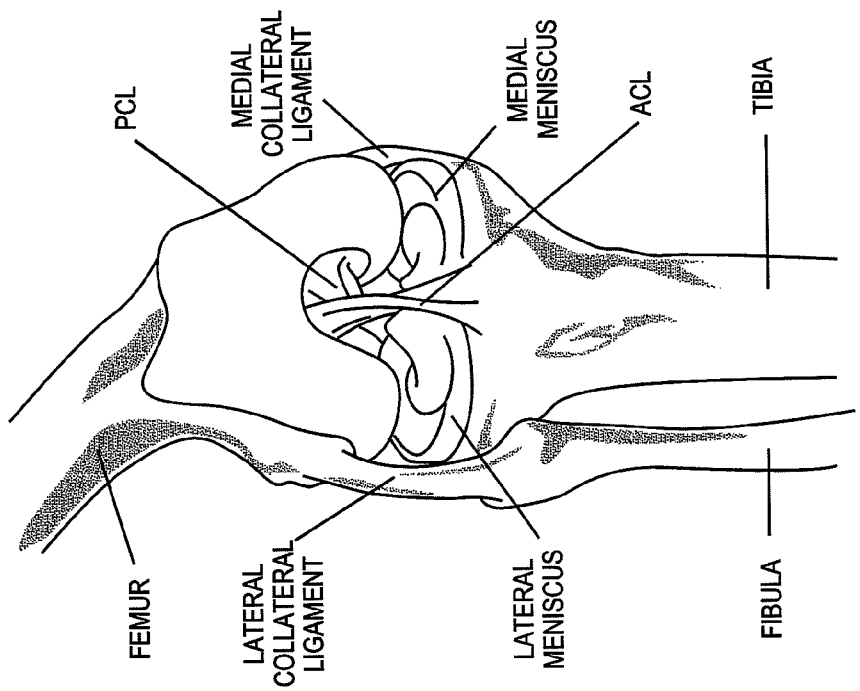
Figure 3:
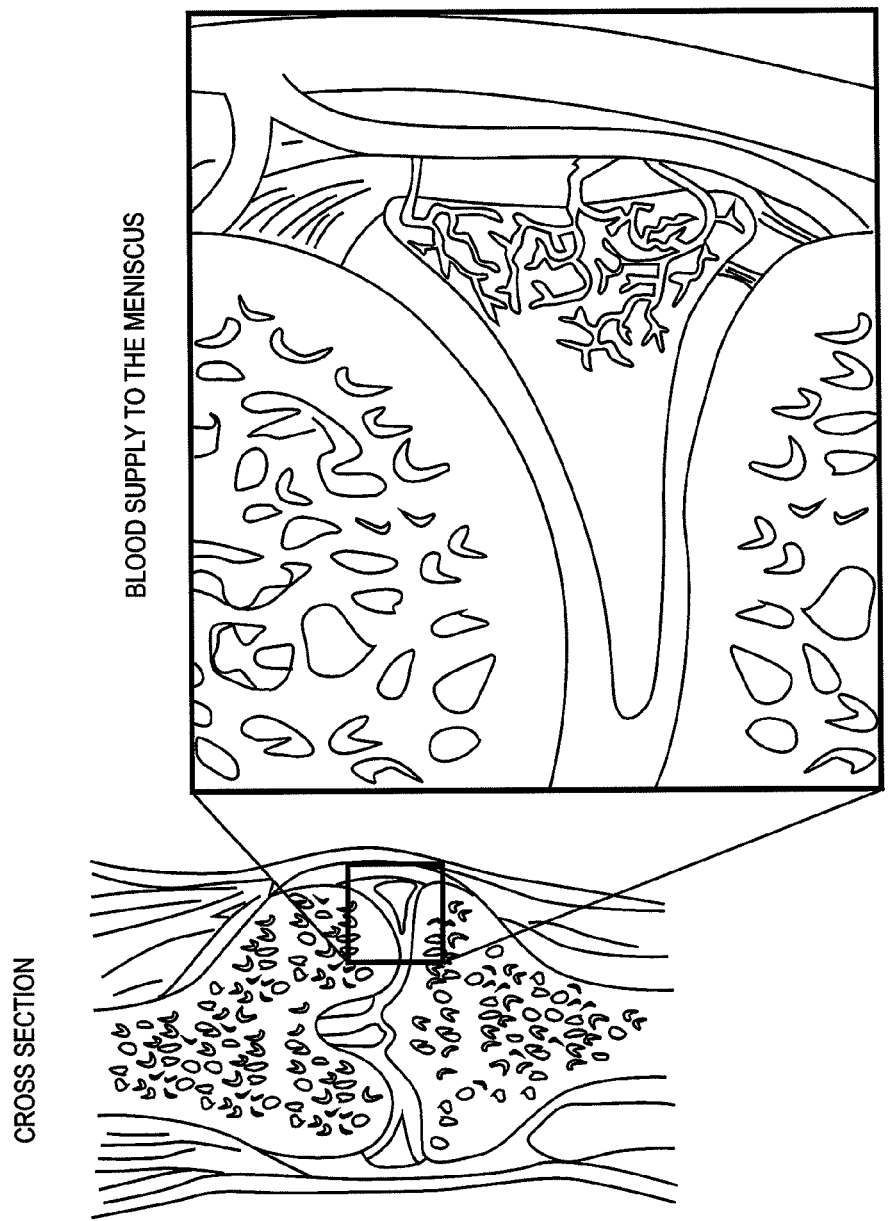
FIG. 3 illustrates the anatomy of the meniscus, including the capsule and associated vascular tissue.
Figure 4:
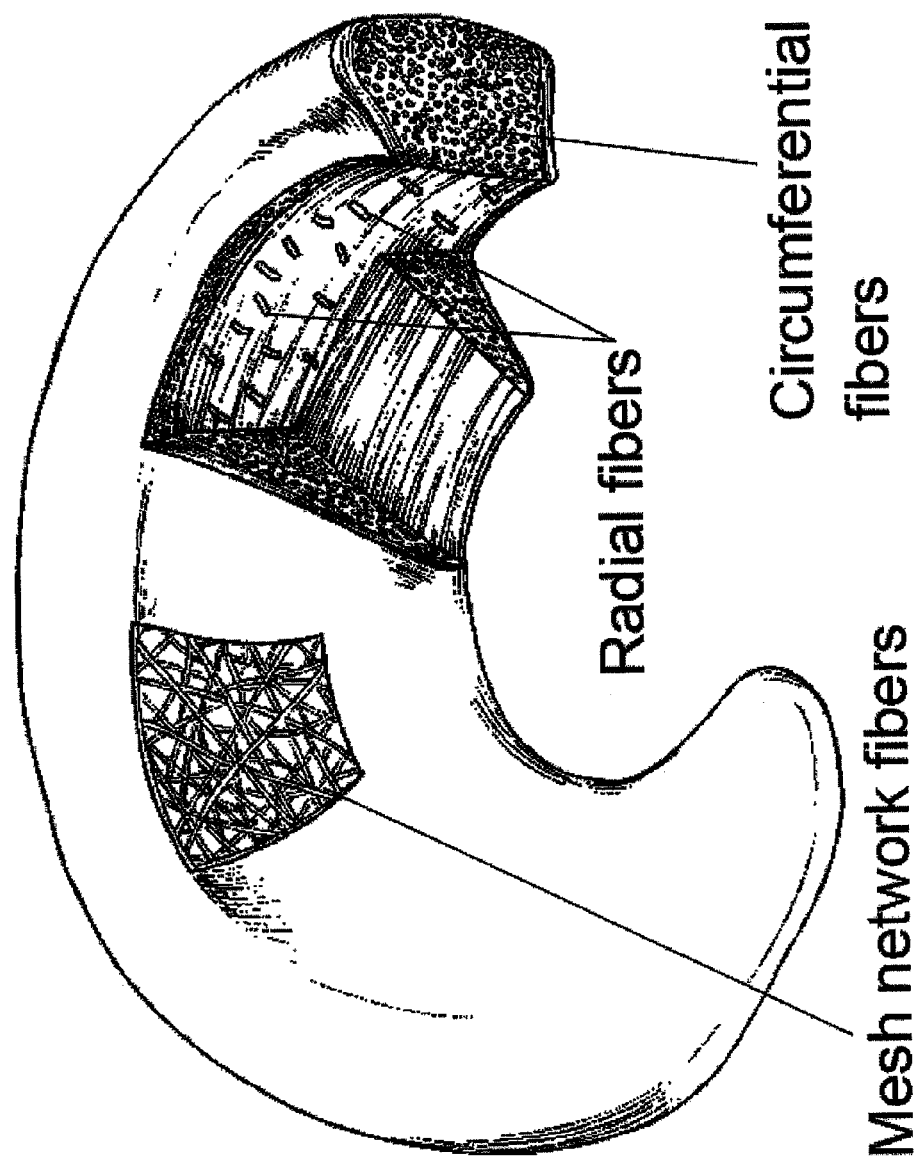
FIG. 4 illustrates the structure of a meniscus.

In FIG. 1J, the first arm (and thus the device) is withdrawn axially (proximally), so that the device may be removed, as shown in FIG. 1K. Removing the device leaves the suture passed through the meniscus, as illustrated in FIG. 1L. The suture may be drawn through the tissue, leaving the loop through the tissue behind. A knot may then be tied or the suture may otherwise be secured, as illustrated in FIG. 1M. A pre-tied knot may be pre-packaged to slide into place as the device is withdrawn.

Figure 6C:
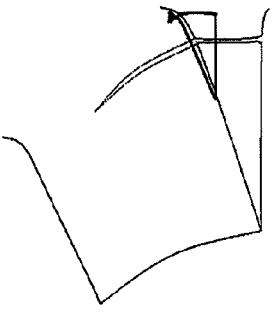
FIG. 6A-6C illustrate meniscus repair using prior art devices.
Figure 6D:
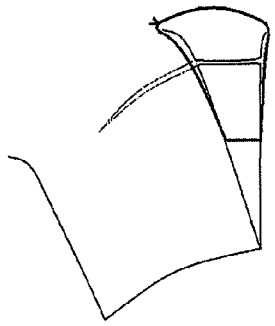
FIG. 6D illustrates meniscus repair using a device as described herein.
Figure 6A:
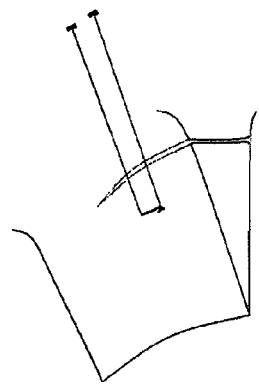
Figure 6B:
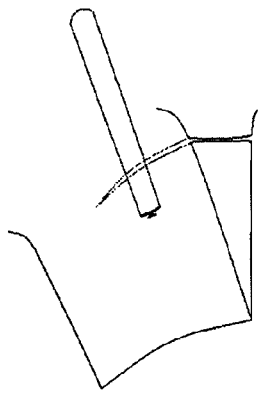

FIG. 6D illustrates one variation of a suture made through a region of the meniscus having a longitudinal tear. The resulting suture may be compared with other types of suture fixations ("stitches") made by other devices, as discussed in the background section above, relative to FIGS. 6A-6C. In comparison, the meniscus suture devices described herein may pass a suture through the meniscus near the boundary (or just past the boundary) of the capsule region (to the right of the figure in FIG. 6D). Because the device may pass the suture vertically through the meniscus (as illustrated in FIGS. 1A-1M), and because of the orientation and configuration of the tissue penetrating element, the suture may be passed without risk of plunging deep into and beyond the capsule region of the knee. This design may prevent injury to nearby nerves and vascular tissues (e.g., blood vessels). In addition, the suture maybe passed over and around the outside regions of the capsule, as illustrated.

FIG. 7A illustrates one variation of a meniscus repair suture passer. In this example, the suture passer includes an upper ("second") jaw or arm that extends longitudinally from the elongate body and curves up (out of the longitudinal axis) as illustrated. The lower "jaw" or arm (first arm) member is slideable relative to the upper arm, and can be extended in the longitudinal axis of the device and held in any of three positions, as illustrated in FIGS. 7B-7D. These positions are labeled "$1^{st}$ position," in which the lower arm is fully retracted, as shown in FIG. 7B. A control, slider member (shown as a finger or thumb slider in FIG. 7A), may be used to axially move (e.g., slide) the lower arm forward or back (or to hold the lower arm stable while moving the rest of the device forward/back relative to the lower arm). The second position, shown in FIG. 7C is fully extended. As mentioned, the device may include a lock or bias to hold the arms in this position once slid or otherwise moved here. For example, the device may include a spring-lock that can be engaged (releasably) to hold it in position, allowing the tissue penetrator to be extended or retracted as described above. Finally, FIG. 7D illustrates a third, intermediate, position of the first arm, which may also be locked, and for which a corresponding mating site (e.g., docking site) for the tissue penetrating element may also be present. The intermediate position ($3^{rd}$ position) may be optional. In some variations additional intermediate positions may also be included.

Figure 8:
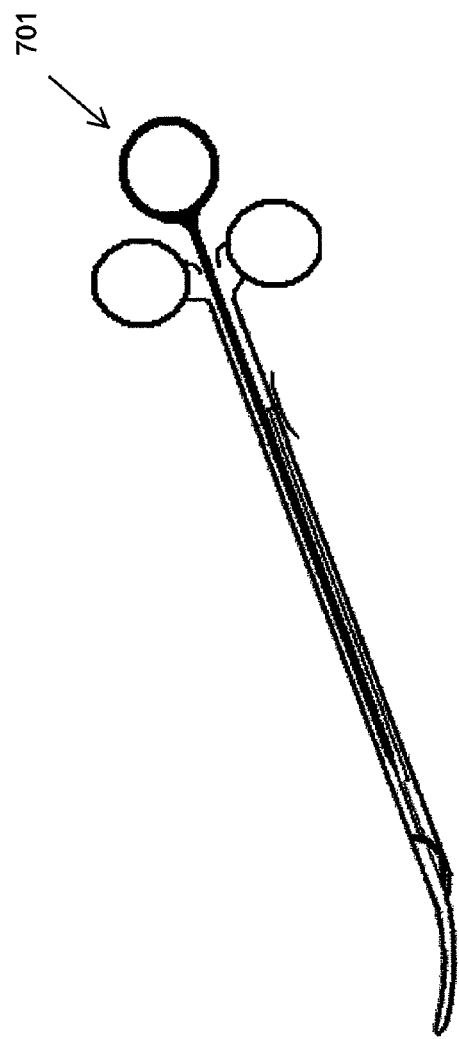
FIG. 8 shows another variation of a meniscus repair suture passer as described herein.

A separate mechanism may be used to extend/retract the tissue penetrating element from the lower arm to engage the upper arm. For example, a trigger may be included. In FIG. 7A and FIG. 8, the device includes a push element 701 within the cannula of the elongate body that allows the tissue penetrating element to be extended/retracted. As mentioned the device may be configured to prevent the tissue penetrating element from extending (or retracting) when the arms forming the opening are not aligned so that tissue penetrating element will not extend unless it can engage a shuttle dock region (and couple with/release the suture shuttle and/or suture). For example, the tissue penetrator may be allowed to extend from the device only when the lower arm is in the second or third positions.

The shuttle dock region may be configured to alternatively lock (hold) and release the suture shuttle, depending on whether the suture shuttle is already present within the dock. This may allow the suture (and shuttle) to be released or retained by dock/tissue penetrator and pulled through the tissue alternatively, allowing continuous suturing.

Figure 9A:
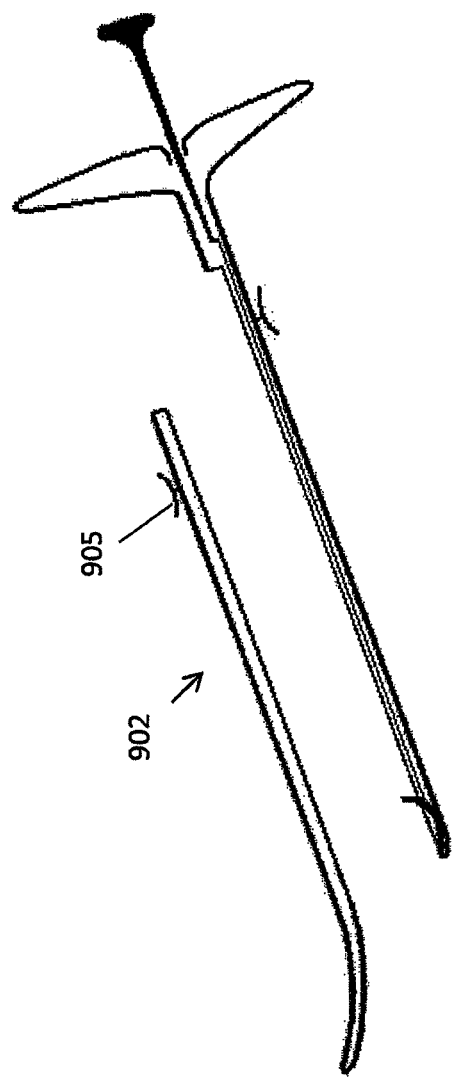
FIG. 9A shows one variation of a meniscus repair suture passer.

In some variations, the upper or lower arm is removable or replaceable. For example, the device may be modular. FIGS. 9A and 9B illustrates variations of meniscus suture passer devices having a modular design allowing various upper arms to be connected to the rest of the device, as shown in FIG. 9C. In this example, the principles of which may be generalized to other variations (e.g., in which the lower arm is replaceable), the upper arm may be pre-loaded with a suture (which may be coupled to a shuttle). Different, interchangeable, upper arms may be used that include different structures. For example, different upper arms may have different bend angles of the arm relative to the long axis of the device (e.g., between 10 and 60 degrees, as indicated above). In some variations the device may have different lengths, widths, and/or thicknesses. In some variations different upper arms may be selected based on the number and/or locations of the shuttle docks on the arm. Although this section refers to the jaw or arms as the modular or interchangeable feature of the device, the actual interchangeable region may include the bent distal end region of the upper arm and the un-bent elongate portion, as seen in FIGS. 9A and 9B. In this example, the interchangeable region 902 also includes a grip region 905 that may be used to couple the second arm to the rest of the device, and may be useful in variations in which the upper arm (second arm) is axially movable relative to the handle. FIGS. 9B and 9C illustrate this variation in slightly more detail, showing the disposable and preloaded upper arm 902 and a potentially re-usable or durable lower arm that may be combined to form the meniscus suture passer device 900 shown in FIG. 9C. The durable portion may be sterilizable so that it can be re-used with multiple patients, or it may be merely used to pass multiple sutures for a single patient.

In operation, a user may measure or probe the meniscus region (including non-invasive imaging) to determine which upper arm to select. The upper arm may then be coupled with the rest of the device, including the lower arm and handle. The upper arm may be coupled to the rest of the device by a snap-fit, a lock, and/or any other mechanical, magnetic, etc. connection means that may be used to link the upper arm with the rest of the device.

As mentioned above, in some variations the upper arm is held relatively stationary relative to the rest of the device (e.g., the handle, elongate body, etc.) and the lower arm is axially extended/retracted. In some variations, including the variation shown in FIGS. 9A-9C, the upper arm is axially extendable/retractable. For example, the upper arm may be attached to the meniscus repair device and allowed to slide forward or retracted. The lower arm may also be configured to slide axially, or it may be held fixed relative to the rest of the device (e.g., the handle region).

Figure 10A:
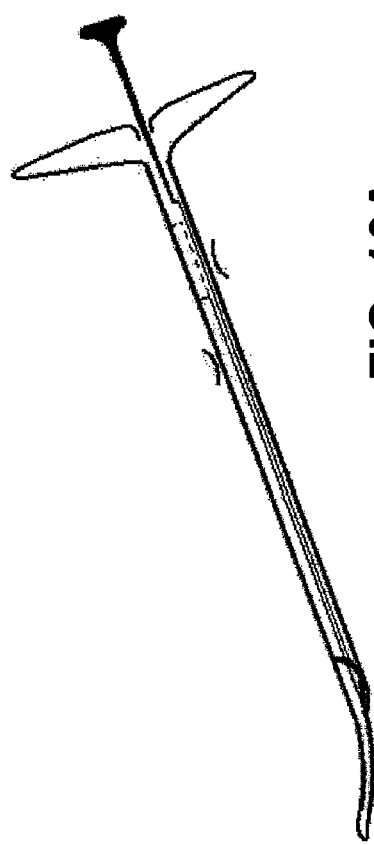
FIGS. 10A and 10B illustrate one variation of a meniscus repair suture passer.
Figure 10B:
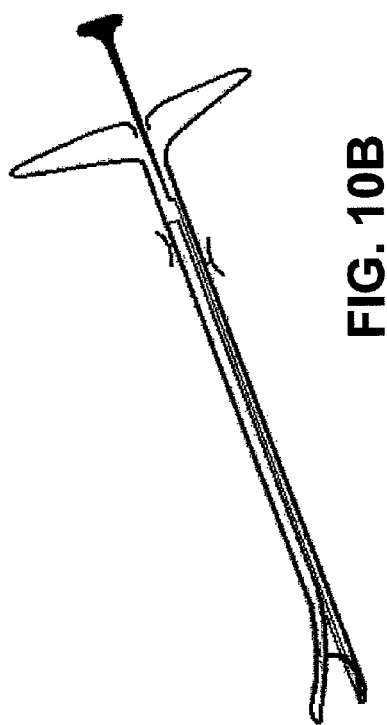

FIGS. 10A and 10B illustrate another variation of a meniscus suture passer device in which the upper and lower arms may be moved axially and individually locked into position.

Figure 10C:
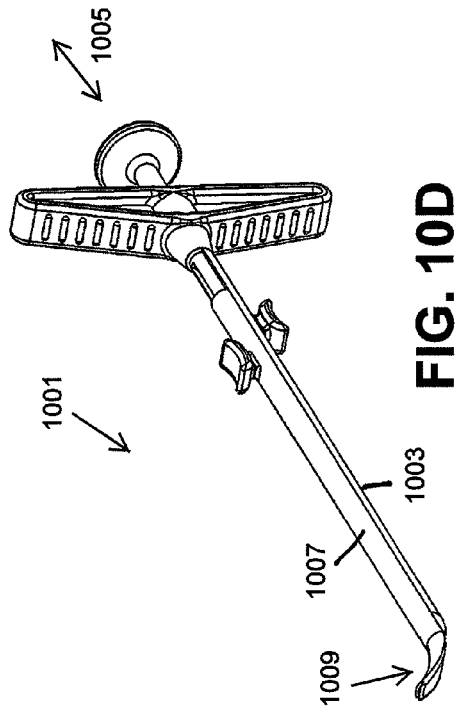
FIGS. 10C and 10D show a meniscus repair suture passer from two different side perspective views in which the upper (bent) arm extended and the lower (straight) arm retracted.
Figure 10D:
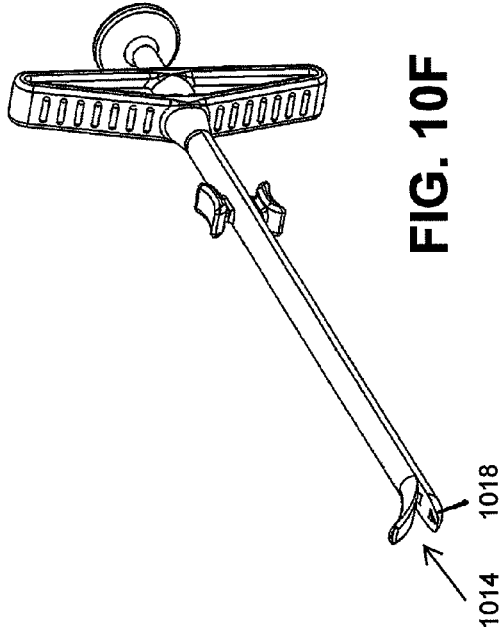

The various configuration of the upper and lower arm relative to each other in one variation of a meniscus repair suture passer device are illustrated in FIGS. 10C to 10H. For example, FIGS. 10C and 10D illustrate two perspective views of one variation of a meniscus repair suture passer device 1001 having an elongate first arm 1003 that is axially movable (in the dorsal/proximal long axis of the device 1005) relative to the rest of the device, including a second arm 1007. The elongate second arm 1007 extends adjacent to the first arm along the long axis 1005 of the device. The elongate second arm also includes a bent distal end region 1009 that may be bent relative at an angle relative to the long axis of the device, as shown. The distal tip of this distal end region is atraumatic, and is shown as substantially blunt. In FIGS. 10C and 10D, the first arm is retracted proximally so that it does not form a distal opening in this position.

Figure 10E:
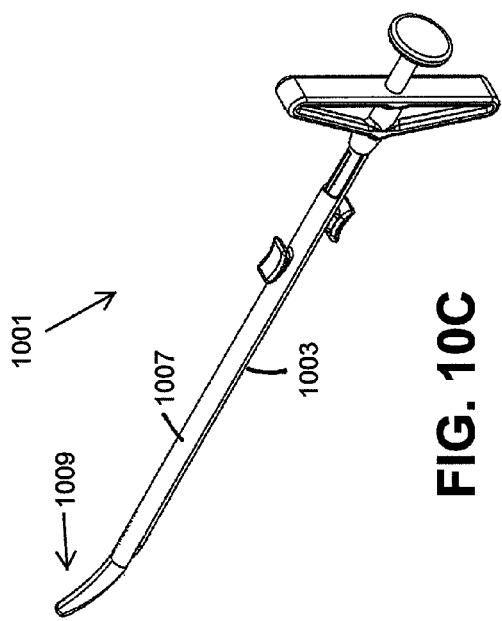
FIGS. 10E and 10F show the meniscus repair suture passer of FIGS. 10C and 10D after the lower (straight) arm has been extended.
Figure 10F:
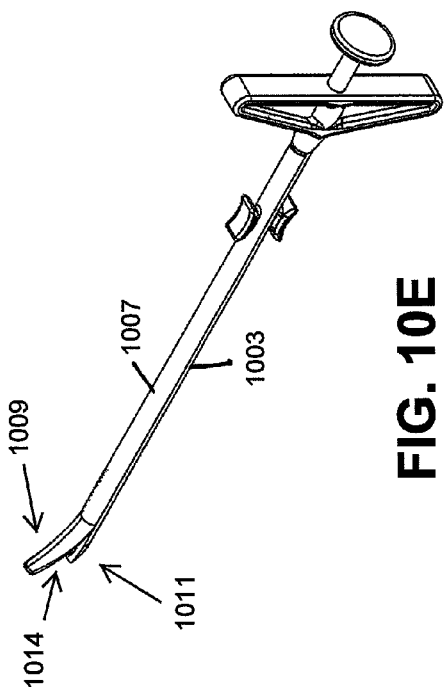
Figure 10H:
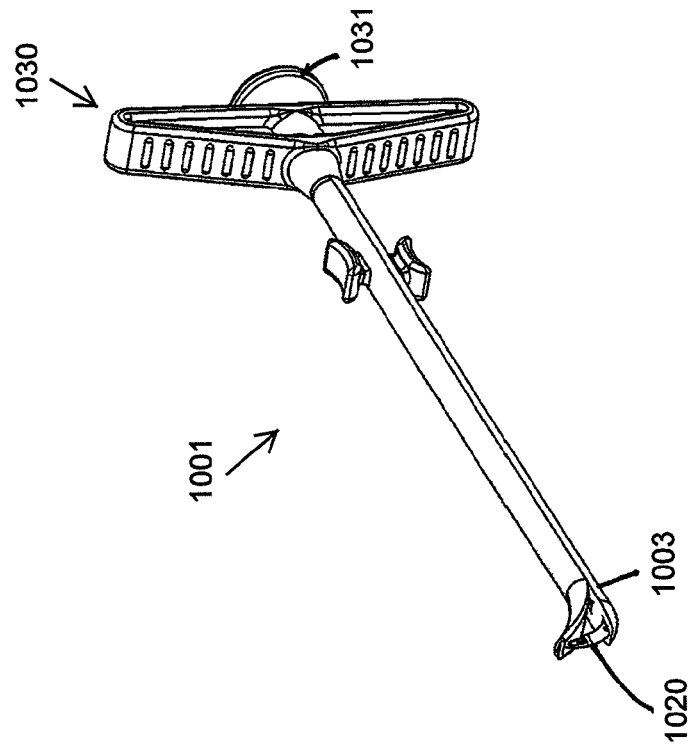
FIGS. 10G and 10H show the meniscus repair suture passer of FIGS. 10C and 10D after the lower (straight) arm has been extended and the curved tissue penetrator has been extended.
Figure 10G:
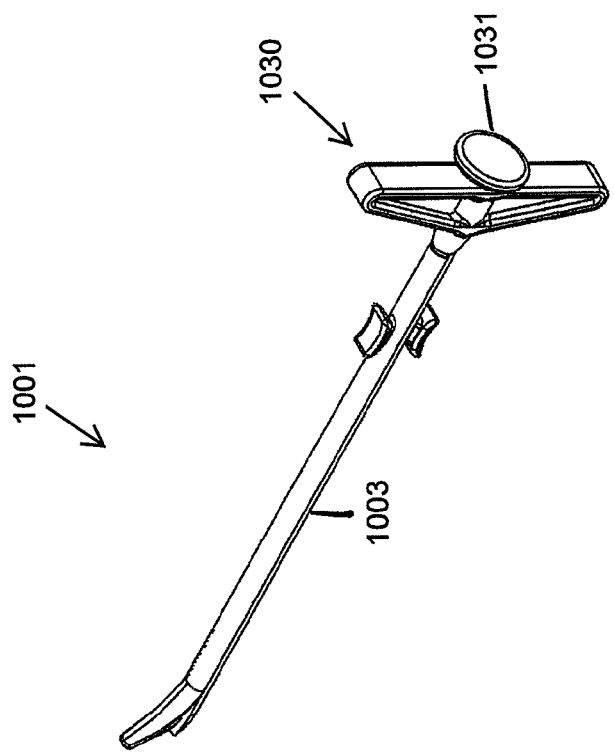

FIGS. 10E and 10F illustrate an extended position in which the distal end region of the first arm 1011 has been extended distally towards the distal end region 1009 of the upper arm (second arm 1007). The distal end regions of the first and second arms 1009, 1011 have formed a distal opening between the first and second arms 1014. The exit for the tissue penetrator is visible as an opening 1018 in the lower arm 1003 in FIG. 10F. FIGS. 10G and 10H show the same views of the suture passers 1001 shown in FIGS. 10E and 10F, but with the tissue penetrator 1020 extended from the first (lower) arm 1003. The tissue penetrator may extend in a curved path through the tissue between the first and second arms, as shown. All of the devices shown in FIGS. 10A-10H include a handle 1030. In FIGS. 10G and 10H a control 1031 on the handle 1030 is shown as depressed, actuating the extension of the tissue penetrator 1018 between the upper and lower arms.

Figures 5A, 5B, 5C, 5D, 5E:
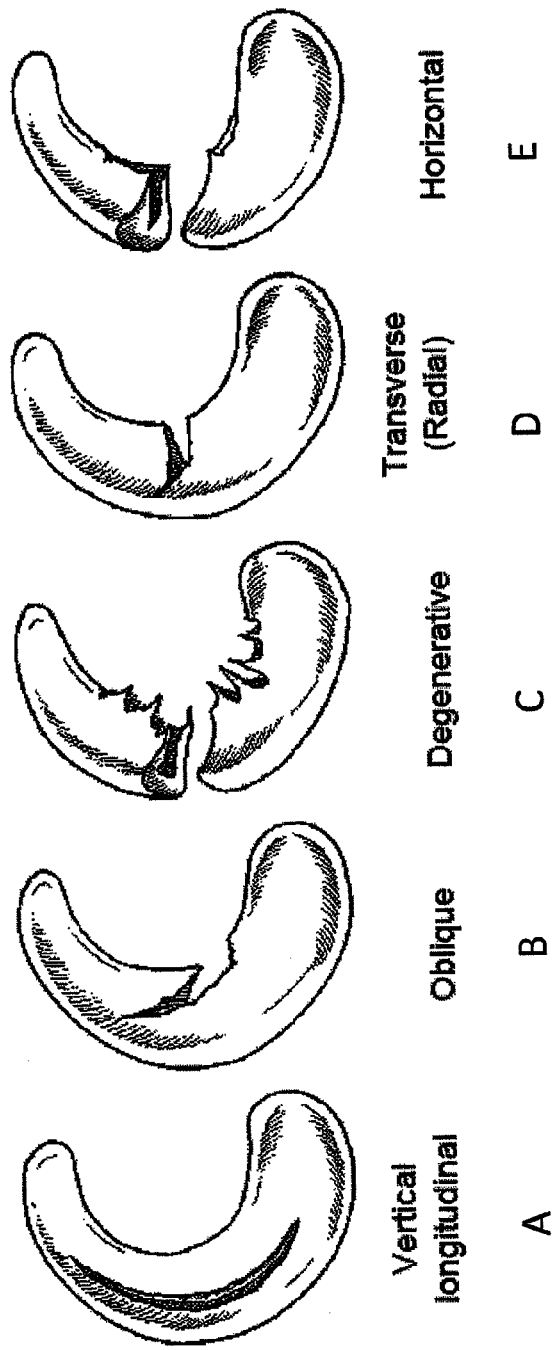
FIGS. 5A-5E illustrate various tear patterns that may be repaired using the invention described herein.

As described, the meniscus repair suture devices described herein may be used to repair longitudinal meniscus tears (e.g., FIG. 5A). The configuration of the arms (which move axially in the long axis of the device) and the tissue penetrator element (which is configured to extend substantially perpendicular to the lower arm), of the devices described herein may also be used to repair radial or even oblique tears in the meniscus (e.g., FIGS. 5B-5E). Repair of such tears is typically difficult or impossible using other prior art devices. Repair of such radial and oblique peripheral tears is made possible because the suture passer described herein may pass suture from the superior (upper) to the inferior (lower) surface of the meniscus (or vice versa). Repair of radial and oblique tears is also made simpler and more convenient because the meniscus suture passer devices described herein may continuously pass a suture between the upper and lower arms without having to be removed from the tissue. This is illustrated in FIGS. 11A-11i.

Figure 11A:
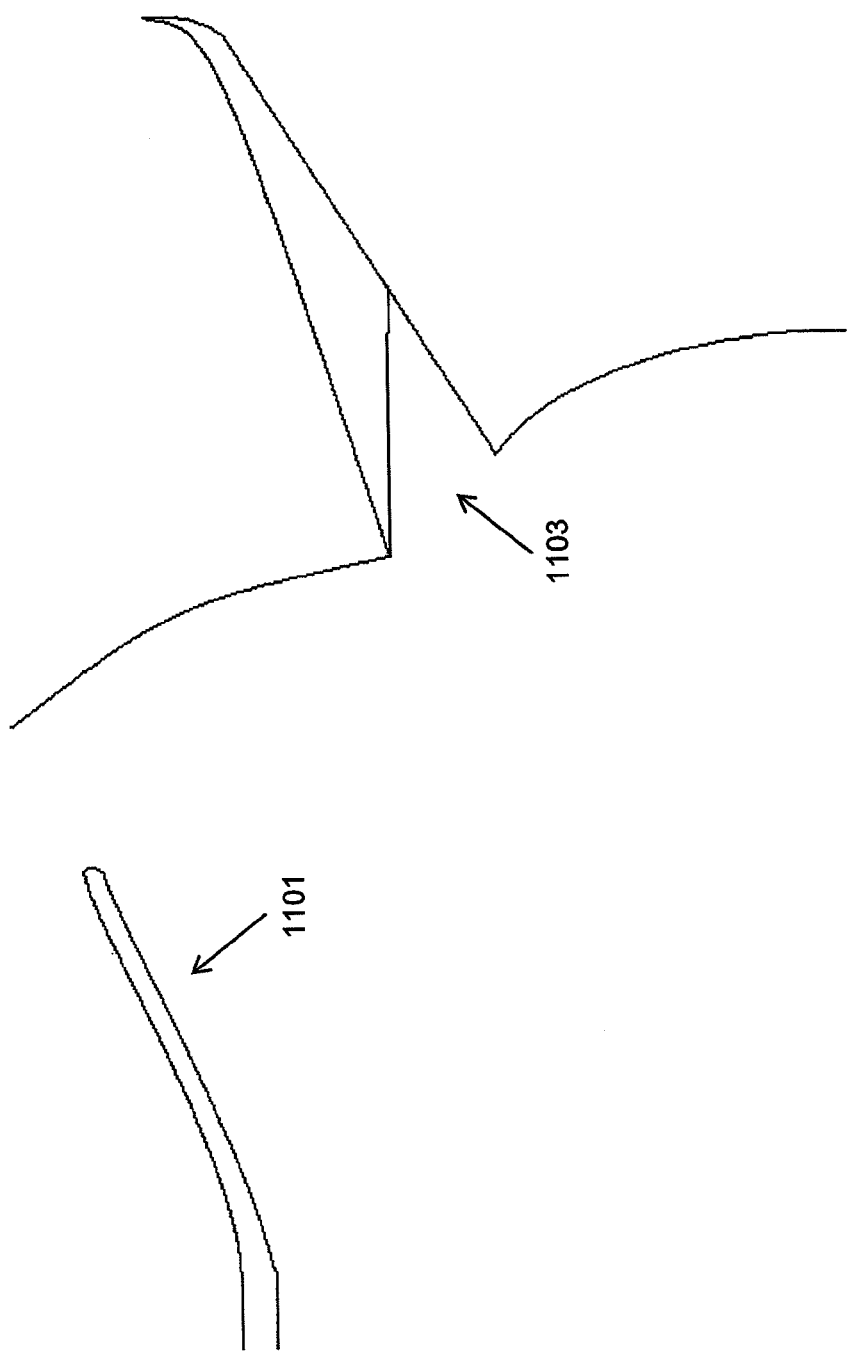
FIG. 11A-11i illustrate use of a meniscus repair suture passer repairing a radial tear in a meniscus.
Figure 11B:
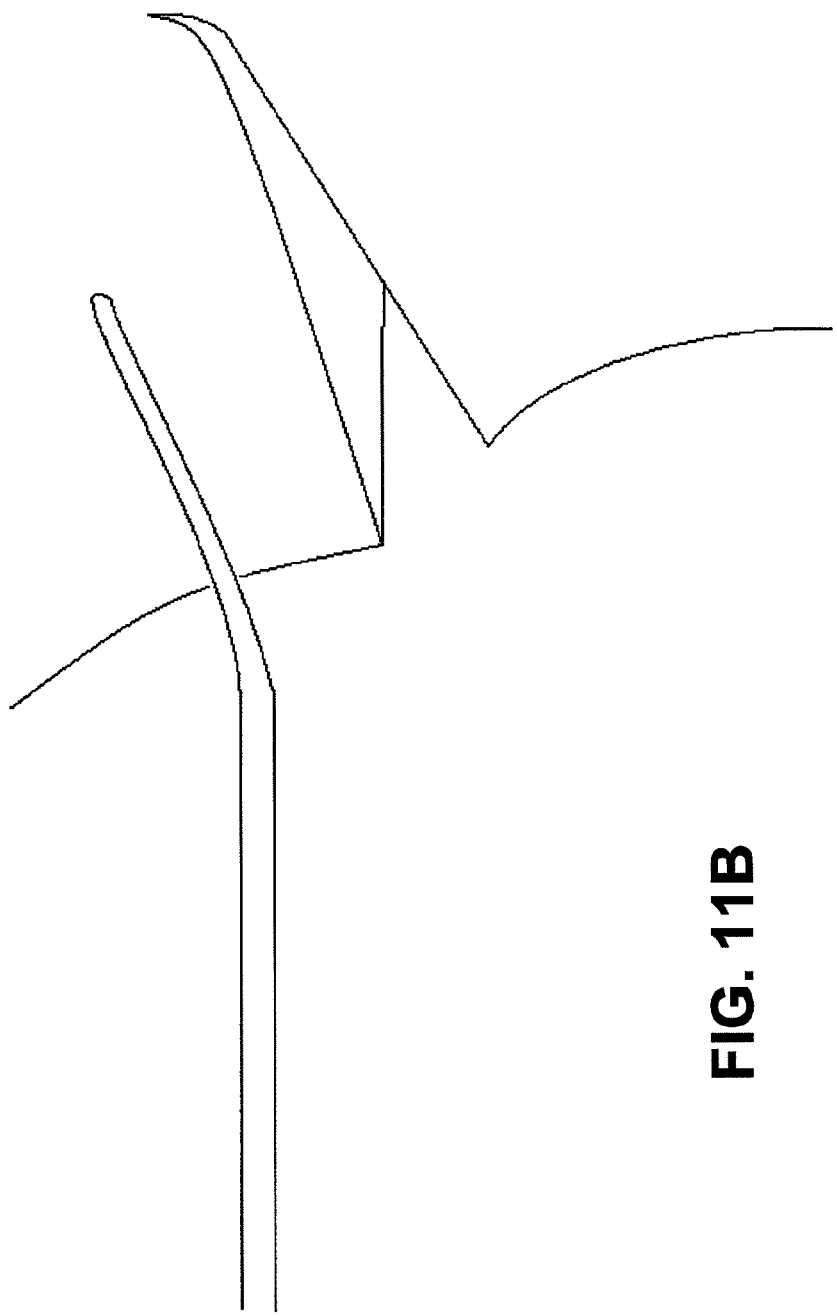
Figure 11C:
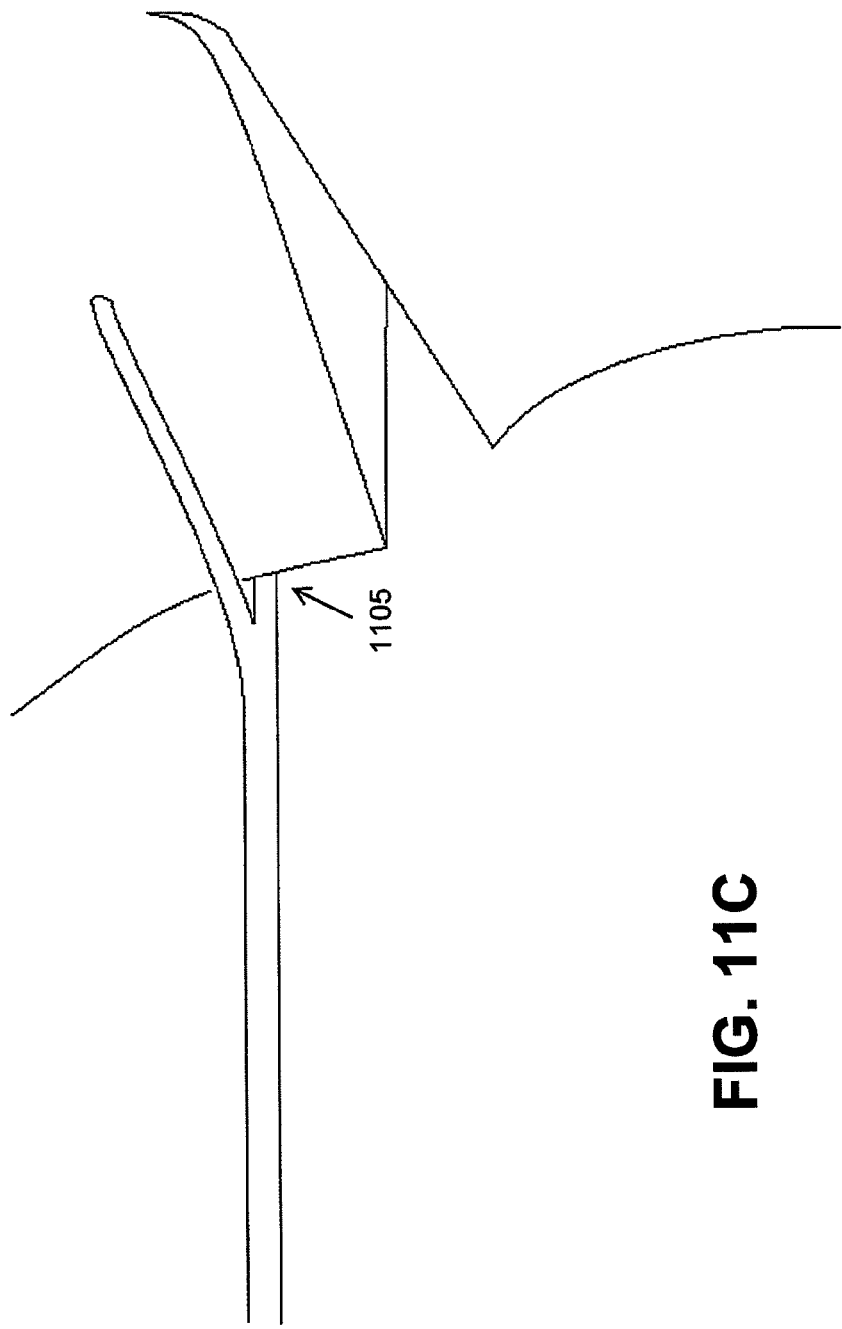

FIGS. 11A-11i illustrate one variation of a method of repairing a radial meniscus tear using one variation of a meniscus repair suture passer device as described herein. FIGS. 11A-11B shows the distal end of a suture passer (the curved/bent distal end of the upper arm of the device) 1101 approaching a region of a meniscus having a radial tear 1103. The distal tip of the upper arm may be maneuvered to fit within a minimal incision and may follow along the contour of the upper surface of the meniscus. Once the upper arm is positioned, the lower arm 1105 may be extended under the meniscus, as shown in FIG. 11C. In this example, the lower arm is fully extended, and then the tissue penetrating element is extended through the tissue. The tissue penetrator may extend through the meniscus and/or through the capsule region. In this example, the lower arm is pre-loaded with a suture attached to a shuttle and held on the tissue penetrator. In some variations the upper arm is pre-loaded, with the suture and shuttle held in a shuttle receiver/dock at the distal end region of the upper arm. In FIG. 11C, extending the tissue penetrator until it engages with the shuttle in the shuttle dock on the upper arm causes the shuttle to secure onto the tissue penetrator and be released from the shuttle dock. Any appropriate tissue penetrator may be used. For example, the tissue penetrator may be a solid curved needle-like element having a triangular cross-section that engages with the inside of a shuttle "clip" connected to the suture. In this example, the suture and shuttle are initially held on the tissue penetrator (clipped on) and the suture is pulled through the tissue as the tissue penetrator is extended through the tissue. Once the tissue penetrator engages the shuttle receiver/dock on the upper arm, it may engage the shuttle receiver and toggle the dock/receiver to secure the shuttle within the receiver, allowing it to be unclipped from the tissue penetrator.

In general, engagement of the tissue penetrator with the shuttle region may toggle engagement or release of the shuttle dock/receiver from the upper arm. This toggling may allow the upper arm to hold or release the shuttle from the dock/receiver; toggling may therefore pre-set the dock/receiver it to either release or receive the shuttle during the next engagement with the tissue penetrator. Thus, the shuttle dock/receiver may have a mechanical "memory." Alternatively, the shuttle dock may be configured so that if it already has the shuttle present it will release it, and if it does not have the shuttle it will capture it from the tissue penetrator. This toggling may be individually controlled for all of the shuttle docks on the upper arm if more than one is present), or it may be collectively controlled. Thus, in some variations each of the shuttle docks may be loaded with a separate suture, allowing multiple sutures to be passed without having to remove and re-load the device, by using separate shuttle docks/receivers on the upper arm.

Figure 11D:
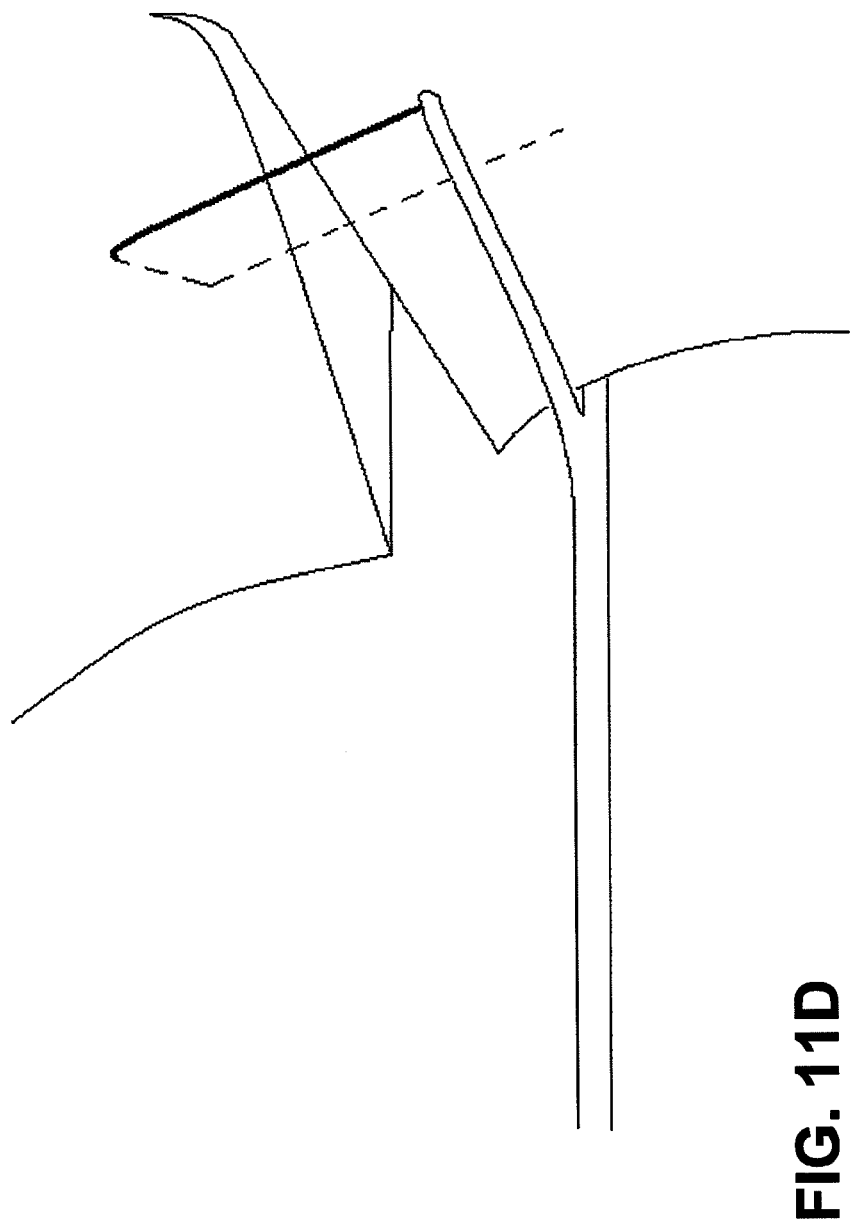

Once the suture is passed from the lower arm (via the tissue penetrator) to the upper arm, the tissue penetrator may be retracted back the lower arm, leaving the shuttle and suture in the upper arm, and the device may be moved laterally relative to the meniscus, as shown in FIG. 11D. Lateral motion of the distal end of the device across the radial tear, as illustrated, will pull the suture from the lower arm (e.g., where it may be held loosely within a lumen of the device (e.g., in the lower arm or a cannulated region of the device body) and through the tissue to follow the upper arm. The suture remains attached to the suture shuttle, and therefore follows it as the arms are moved relative to the tissue. The dashed lines show the path of the ends of the device in FIG. 11D.

Figure 11E:
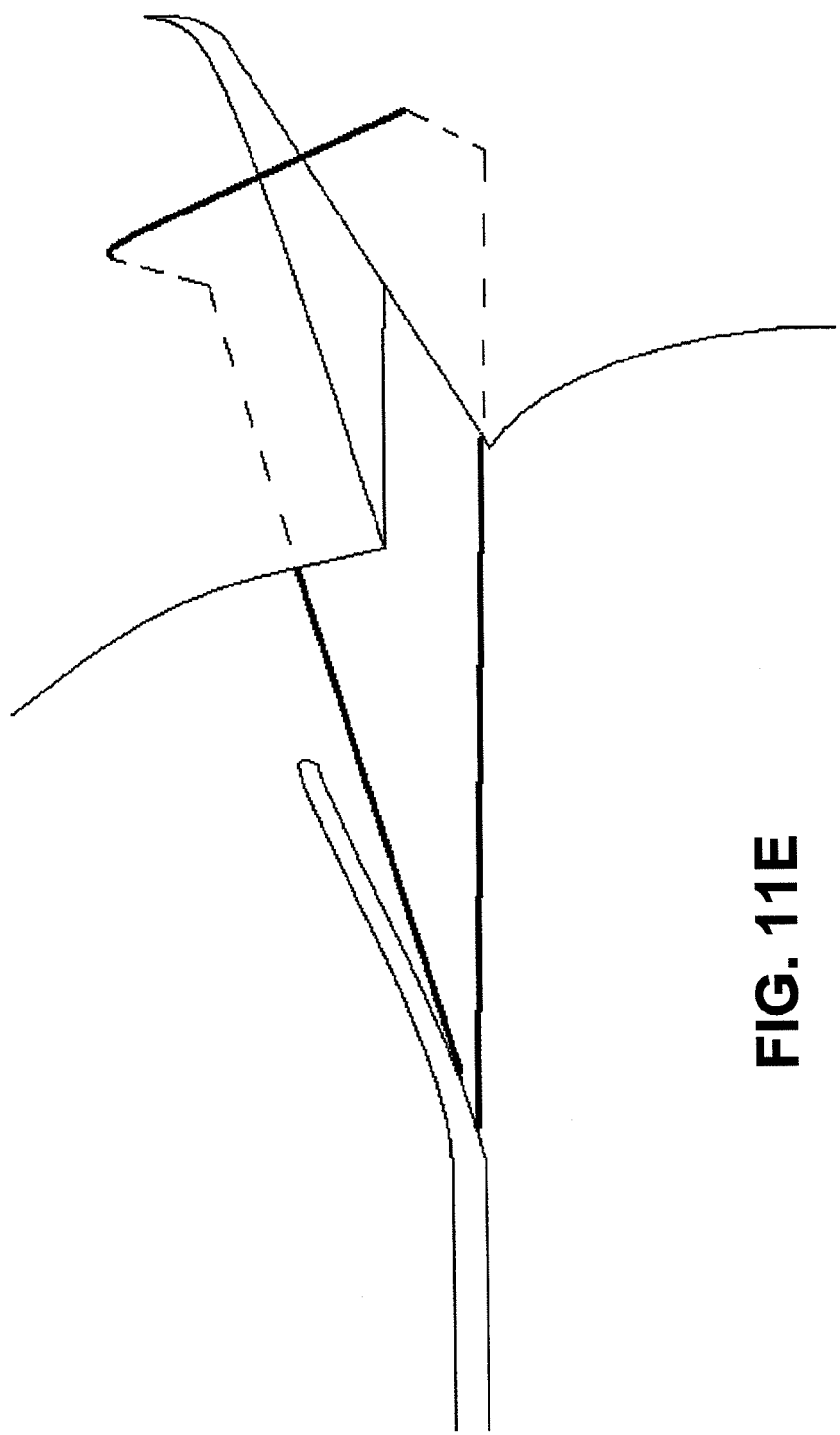

Generally, the suture may be managed by the device. The suture may be held loosely within a lumen of the device (e.g., within the upper arm, elongate body region of the device, lower arm, etc.) so that it may be fed out of the device and allowed to pass through the tissue easily. In other variations the suture is not held within the device, but it either freely connected (e.g., hanging from the distal end of the device), partially held within the device, fed through a loop of wire or suture from the device, or kept in a track or guide along the outside of the device (or some combination thereof). In FIG. 11E, the suture is shown extending from the elongate body of the device. In other variations the suture may be held in the upper arm, particularly when preloaded in the upper arm. The device (including the upper arm, elongate body, lower arm, etc.) may include one or more lumen or passages for the suture, which may include exits (e.g., side exits) for managing the pathway of the suture as it is passed through the tissue.

Returning to FIG. 11D, once the distal end of the device has been positioned on the other side of the meniscus tear, the tissue penetrating member may again be extended through the tissue (e.g., through the meniscus, capsule, etc.) where it can again engage with the shuttle and/or suture, causing the shuttle to be disengaged from the shuttle dock/receiver on the upper arm. The shuttle and suture are then coupled to the tissue penetrator (e.g., by snapping the shuttle onto the tissue penetrator) and the tissue penetrator can be pulled through the tissue, pulling the suture with it though the tissue until the shuttle and suture coupled to the tissue penetrator are withdrawn into the lower arm, allowing it to be withdrawn, as shown in FIG. 11E.

Figure 11F:
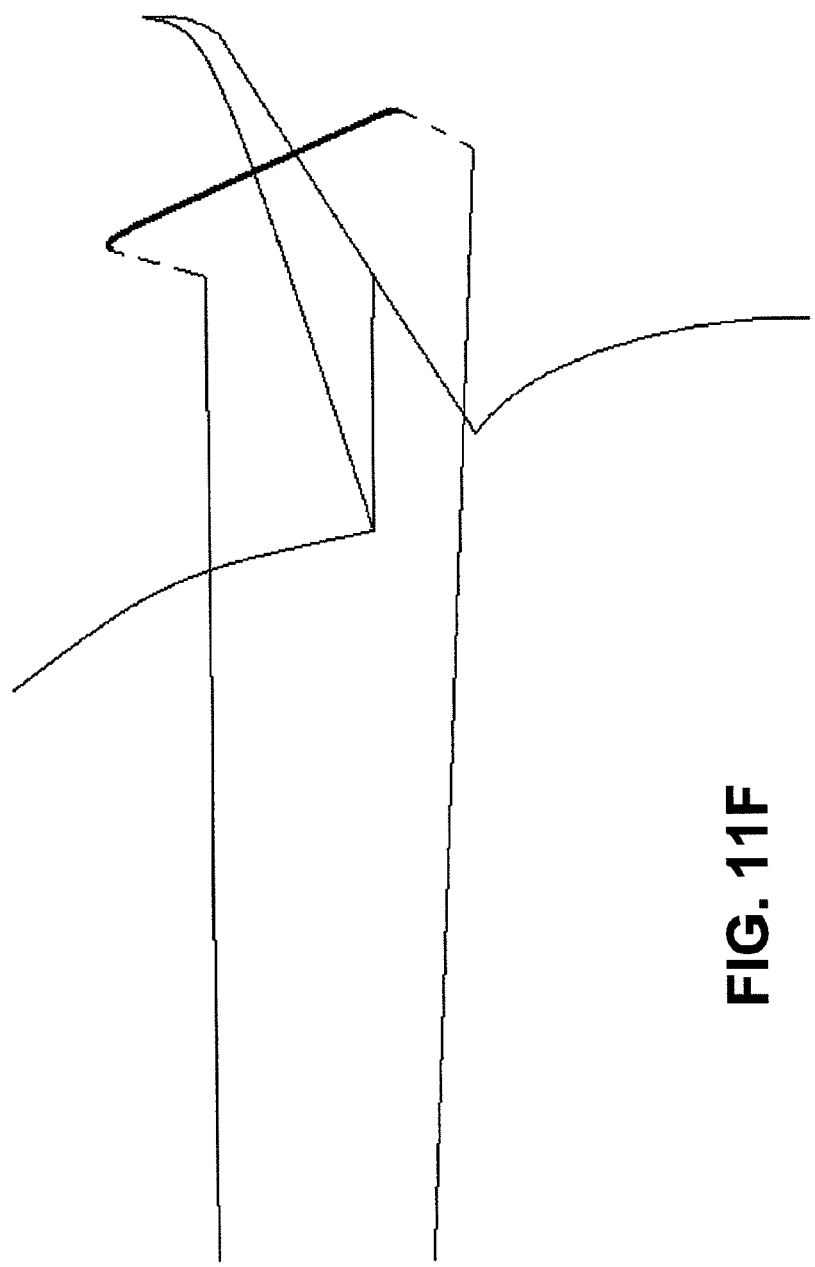
Figure 11G:
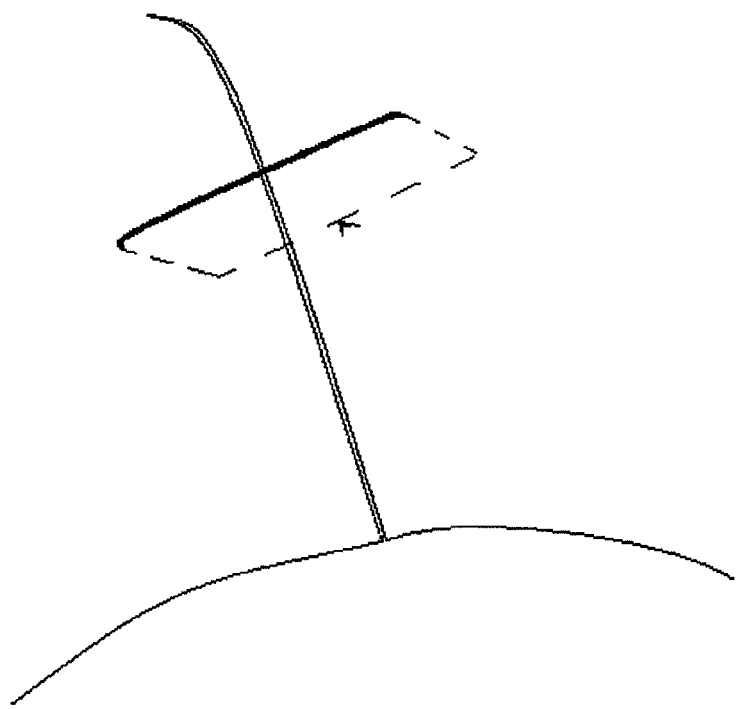
Figure 11H:
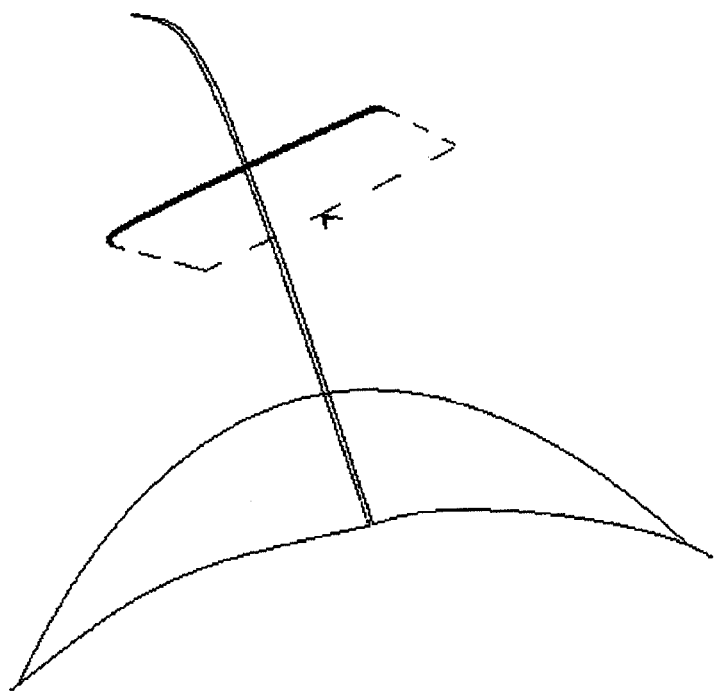
Figure 11I:
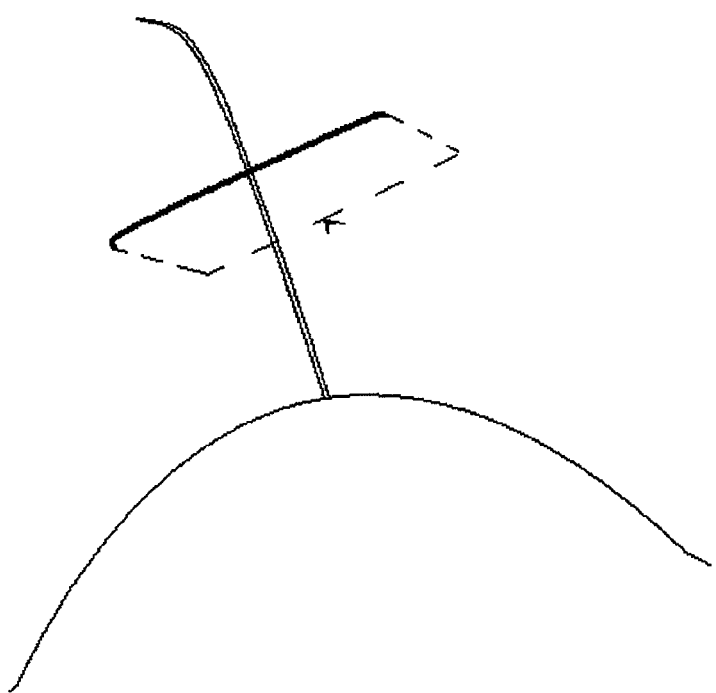

The resulting suture passes through the meniscus on either side of the tear, and the suture extends across the tear, in the mattress-like stitch shown in FIG. 11E. Thereafter, the device can be withdrawn, leaving the ends of the suture trailing, as illustrated in FIG. 11F, allowing the suture ends to be tied across the tear, pulling the side of the torn region of meniscus together, as illustrated in FIG. 11G. The suture may be knotted (directly or using a knotting device), and tied off. Alternatively, a prettied sliding knot may be provided within the device. Thereafter, the less-vascular regions of meniscus (towards the narrower, more apical region) may be removed, as illustrated in FIGS. 11H and 11i.

Figure 12A:
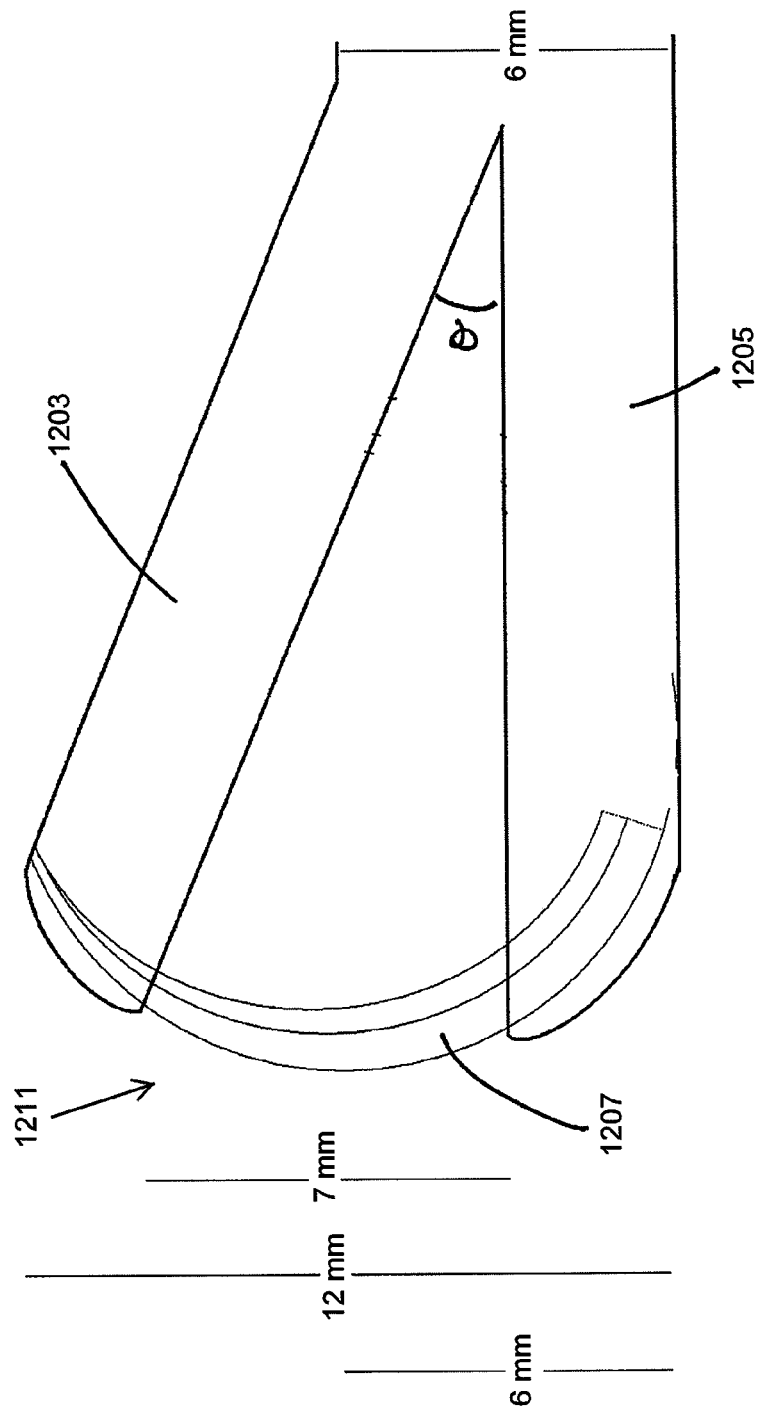
FIGS. 12A and 12B illustrate exemplary dimensions and interaction of the first and second (lower and upper) arms and a tissue penetrator when the first arm is fully (FIG. 12A) and partially (FIG. 12B) extended. The dimensions illustrated are exemplary only, and any of the variations of the device shown herein may be formed having other dimensions, including dimensions that are collectively or individually scaled to be between approximately +/−25% and 200% of the values shown.
Figure 12B:
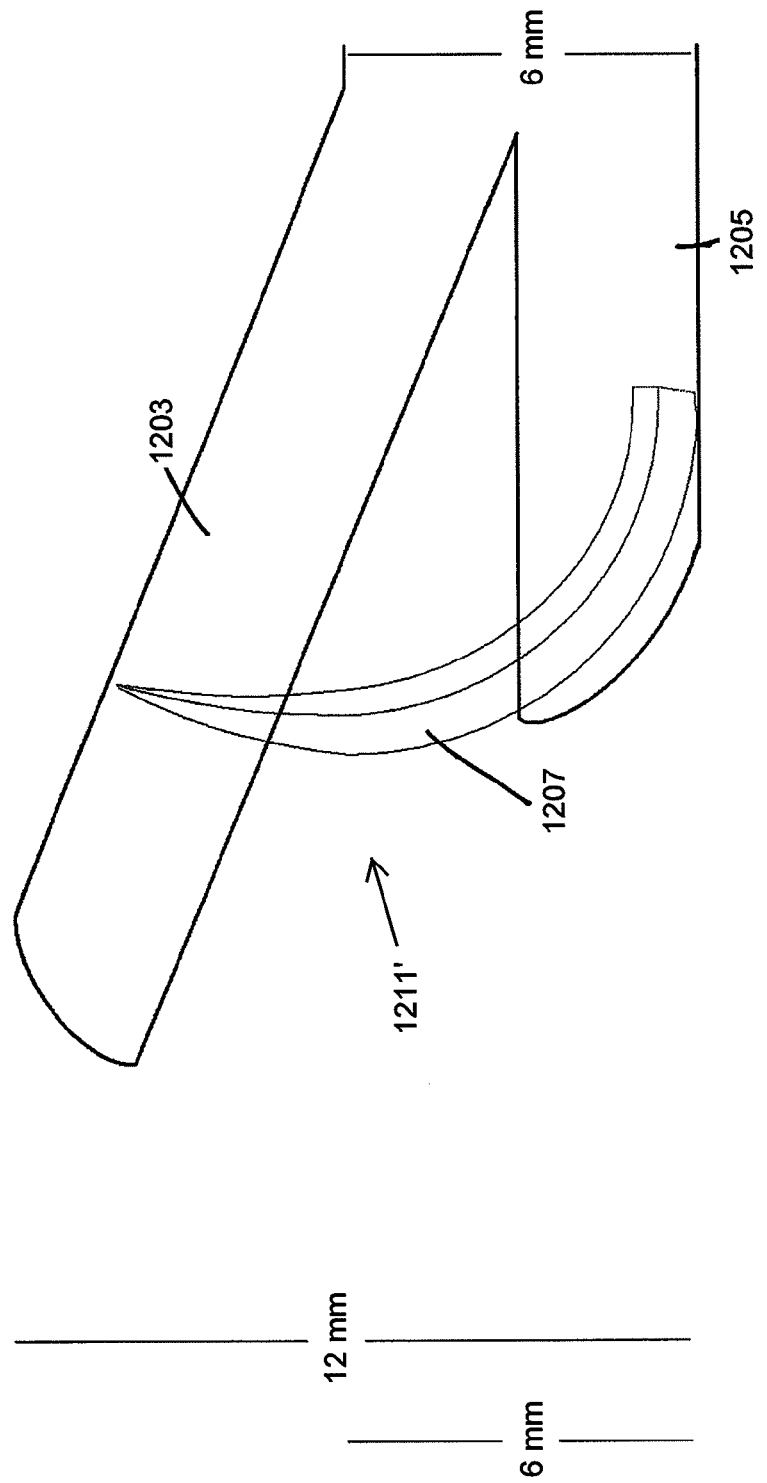

In general, the distal end regions of the lower and upper (first and second) arms may be configured to form a distal opening by sliding the lower (first) arm distally once the upper (second) arm has been positioned on one side, preferably the superior side, of the meniscus. The distal end regions may also be configured so that the tissue penetrator may be able to extend across the tissue within the distal opening from one or more positions. For example, one schematic illustration of a distal opening formed by the distal ends of the first and second arms of a suture passer is illustrated in FIGS. 12A and 12B. These examples indicate exemplary dimensions; these dimensions are intended only to provide one illustration of dimensions that may be used. The suture passer devices making up this invention are not limited to these dimensions.

For example, FIG. 12A shows a lower arm 1205 that is axially movable relative to the upper arm 1205. A tissue penetrator 1207 may be housed within the lower arm completely until it is extended across the distal opening 1211. In this example, the angle between the upper and lower arms (A) is approximately 35 degrees. As mentioned above this angle maybe greater or lesser than 35 degrees by 2 degrees, 5 degrees, 10 degrees, etc. but is generally an acute angle slightly greater than the corresponding angle between the inferior and superior surfaces of most of menisci. In this example, the overall diameter of the shaft region (proximal to the distal end region forming the distal opening) is approximately 6 mm. In general, this diameter may be less than 10-15 mm. In FIG. 12A, the tissue penetrator extends near the distal ends of the first and second arms, so that the tissue penetrator exist the distal end of the lower (first) arm 1205 and travels in a curved path across the distal opening to pass at least partially into the shuttle dock region (not visible) near the distal end of the upper (second) arm 1203. In FIG. 12B, the lower (first) arm 1205 is retracted partially in the proximal direction. In this configuration, the tissue penetrator 1207 may be extended across the distal opening 1211' to engage with a shuttle dock (not visible) on the upper (second) arm 1203. Thus, as described above, by moving the lower arm, the device may make radially different pathways (and thus suture stitches) through the meniscus, without requiring the device to otherwise move. In this example, moving the lower arm may be considered one way to reposition the device relative to the meniscus. In FIGS. 12A and 13B, the shaft diameter is approximately 6 mm, the distal opening from top to bottom is approximately 12 mm, and the tissue penetration at the deepest point is approximately 7 mm, as illustrated on the figures.

In general, the tissue penetrators described may be completely retracted within one of the arms, typically the distal end region of the first arm. In some variations, the needle may be curved. In other variations it may be desirable to have the needle assume a curved shape upon leaving the arm. For example, the needle may be pre-biased or bendable into a curve that permits it to extend across the distal opening formed between the arms in a curve. FIGS. 13A and 13B illustrate one variation of a curved needle (FIG. 13A) that may straighten out when retracted into the arm, as shown in FIG. 13B. In this example, the needle includes slices 1303 that increase the flexibility of the needle. One side of the needle is solid 1305, so that the needle retains lateral stability. The needle may be formed of a metal (e.g., stainless steel, shape memory alloys such as Nitinol, etc.). FIGS. 14A and 14B illustrate one variation of a needle such as the one shown in FIGS. 13A and 13B retracted into (FIG. 14A) and extending from (FIG. 14B) a lower arm to extend across to the arm forming a distal opening. An axial pushing element (not shown) may be attached to the proximal (non-sharp) end of the tissue penetrator needle to drive it in and out of the lower arm.

FIG. 14C illustrates another variation of a needle that is bendable or curveable. In this example, the needle is hinged 1403. The pivot point allows the needle to be collapsed for retraction into the lower law. Multiple hinged regions may be used. In some variations, the needle may be solid, but may be formed of a shape memory or super/hyper elastic material that assumes the curved shape upon leaving the lower arm.

Any appropriate variation of tissue penetrator and suture shuttle may be used, as mentioned above. FIGS. 15A-20 illustrate some variations of suture shuttles and tissue penetrators. For example, FIGS. 15A-17 illustrate various embodiments of suture shuttle 70, 170 and 270. A suture shuttle 70, 170 and 270 may be any shape such that it may be releasably attached to tissue penetrator 50. While the shape of shuttle 70, 170 and 270 may correspond to the shape of at least a portion of the tissue penetrator 50 for attachment purposes, it may be of any suitable shape. In these illustrative examples, the shuttle is generally triangular in shape, which may correspond to a tissue penetrator 50 having a generally triangular cross-sectional shape. The illustrated examples of suture shuttles are "channel shuttles" which may engage a tissue penetrator 50. For example, a triangular or cylindrical tissue penetrator 50 may be used, as illustrated in FIGS. 18-19D, to which the suture shuttle 70, 170 and 270 is adapted to connect. Tissue penetrator 50 may be, for example, a needle or any like instrument capable of puncturing through tissue. Shuttle 70, 170 and 270 may be substantially hollow within the triangular shape, and may further have a channel 71, 171 and 271, or opening, along a portion of the triangular body. This channel 71, 171 or 271 may serve as an entry way for tissue penetrator 50 to engage the shuttle 70, 170 and 270. Thus, in these embodiments, the shuttle 70, 170 and 270 wraps around a portion of the tissue penetrator 50, which is positioned within the body of the shuttle.

For example, in FIGS. 15A-B, the channel 71 may be positioned on any portion of the shuttle 70. In the illustrated examples, the channel is positioned along an apex of the triangular shape. However, a channel may also be placed along a side of triangular shape or in any other appropriate place.

Some embodiments of shuttle 170, 270 may also contain openings 74 which may make the shuttle lighter, and may also facilitate flexing of the shuttle so that it can readily attach/detach from the tissue penetrator 50. Further, opening 74 may provide an area through which a retaining mechanism, such as a retainer pin 30, may pass to secure shuttle 170, 270.

Some embodiments of shuttle 70, 170 of the present invention may include additional features which may provide controllable, positive, robust, repeatable, and manufacturable retaining structures. Such features may include, for example, protrusions, such as dimples 72, 172 or the like, and finger springs 175 a and b, both of which may help to retain shuttle 170 on the tissue penetrator 50.

The protruding dimples 72, 172 may interact with divots 52, 152 located within a cut-out 51, 151, or recessed portion, of the tissue penetrator 50. The dimples 72, 172 allow for controllable, repeatable retaining of the shuttle 70, 170 on the tissue penetrator 50, whereby the shuttle may, in a preferred embodiment, snap on and off the tissue penetrator repeatedly, as necessary. In a preferred embodiment, the position of shuttle 70, 170 on the tissue penetrator 50 may be the same given an additional feature such as the dimples and divots. In an alternative embodiment, dimples 72, 172 may be located on the tissue penetrator 50, while the divots 52, 152 may be located on the suture shuttle 70, 170.

In a further embodiment, the cut-out 51, in FIGS. 18-19D, may be configured to seat the shuttle against the outer surface of the tissue penetrator, thereby allowing the tissue penetrator to present a uniform outer surface as it penetrates the tissue; meaning the shuttle does not "stick out" from the tissue penetrator, but is flush with the outer surface of the tissue penetrator. This helps keep the shuttle on the tissue penetrator as it extends from upper arm 20 and penetrates tissue.

Additionally, in yet a further embodiment, the upper edge 54 of tissue penetrator 50 may be sharpened to provide additional cutting surface on tissue penetrator. In this variation, the shuttle 70 should not interact with the upper edge 54 such that upper edge 54 is exposed to assist in the piercing action of tissue penetrator.

In a further preferred embodiment, tissue penetrator 50 may include an additional cut-out 51' along a portion of tissue penetrator 50 within cut-out 51. Cut-out 51' may allow additional room for a linkage 85. Cut-out 51' may reduce the chance of damage to linkage 85 during tissue penetrator 50 insertion into shuttle 70, since cut-out 51' may provide additional clearance for linkage 85.

In one embodiment, for example in FIGS. 16A-B and 19A-D, finger springs 175a and 175b may interact with a ramp 153 within the cut-out 151 of the tissue penetrator 150. The finger springs, and even the entire sides of the shuttle 170, may be sloped inwardly towards one end of the shuttle. Thus, in this embodiment, the finger springs are located at the narrowest portion of the shuttle. This slope of the finger springs may interact with the slope of the ramp 153 of the cut-out portion 151. The interaction of these two slopes may regulate the holding force of the shuttle 170 on the tissue penetrator 150 prior to the dimples 172 interacting with the divots 152 to firmly secure the shuttle to the tissue penetrator. Likewise, the holding force is regulated as the shuttle is removed from the tissue penetrator in a similar manner. Thus, when a force is applied to shuttle 170 to pull shuttle 170 off tissue penetrator 150, the finger springs may be forced along the ramp, towards the tip of tissue penetrator, to engage the ramp, causing the finger springs, and thus the sides of the shuttle, to flex apart from one another, and disengage the dimples from the divots.

Continuing with this embodiment, in FIG. 19A, for example, the dimple 172 of the shuttle is engaged with the divot 152 on the tissue penetrator 150. At this point, the finger springs may only be slightly engaged to the tissue penetrator. FIG. 19B illustrates the shuttle 170 beginning to be removed from tissue penetrator. The dimple is no longer in the divot and is instead moving along the surface of the tissue penetrator. The finger springs 175a are increasingly engaged onto the tissue penetrator as they move along ramp 153 within cut-out on tissue penetrator. In FIG. 19C, the finger springs are shown as fully engaged with tissue penetrator, particularly at the point where the ramp ends (at the distal end of cut-out portion). This full engagement may, in a preferred embodiment, cause the shuttle to flex, and as a result widen, such that the dimples are no longer in contact with the cut-out portion of the tissue penetrator. FIG. 19D illustrates the final step wherein the dimple and finger spring are no longer touching the tissue penetrator at all, and the tissue penetrator may be retracted, leaving the shuttle 170 free.

Thus, in various embodiments, the tissue penetrator may be adapted to mate with one or more elements on the suture shuttle, whether it is a dimple, or like protrusion, or finger springs, or the like, that can engage with a divot, depression, cut-out or ramp portion on the tissue penetrator.

Shuttle 70, 170 and 270 may be made of any material suitable for use in surgical applications. In a preferred embodiment, the shuttle must have strength, yet also have sufficient flexibility and resiliency to be able to move on and off the tissue penetrator. Such movement requires the shuttle to flex during removal from and addition to the tissue penetrator. Thus, a suitable spring characteristic may be achieved with a high stiffness material, such as steel, by designing the spring such that it has a high preload characteristic when installed relative to the tolerances. For example, one shuttle design illustrated herein may include retention features that are lower spring stiffness & high preload, which may help provide more consistent performance and decrease sensitivity to tolerances. Note that the intrinsic stiffness of the material (Young's modulus) and the spring constant of the shuttle may be related, but may not be equivalent. In addition, these shuttle designs may have significantly reduced tolerance sensitivity, wherein the tolerance is a small percentage of deflection, compared to other shuttle designs. One suitable material may be stainless steel. For example, the shuttle may be composed of 0.004 in. (0.01 mm) thick 17-7 PH stainless steel, Condition CH-900.

Shuttle 70 may be made of material whose hardness is matched to the tissue penetrator 50. Tissue penetrators of a material that is too hard relative to the shuttle may wear out the shuttle. In one example, the tissue penetrator is stainless steel, Rockwell 60C hardness. The shuttle then may be precipitation hardened stainless steel, "17-4 PH", which is also known as stainless steel grade 630. The shape of the shuttle is matched to the shape of the tissue penetrator, and the shuttle clips onto a portion of the tissue penetrator, and can be slipped on and off repeatedly.

The shuttle 70 may be made of a material having a hardness, stiffness and elasticity sufficient so that it may partially elastically deflect to clamp onto the tissue penetrator 50. In particular, we have found that matching the hardness of the shuttle to the hardness of the tissue penetrator may be particularly important for repeated use. For example, the shuttle may be made of Nitinol, beryllium copper, copper, stainless steel, and alloys of stainless steel (e.g., precipitation hardened stainless steel such as 17-7 PH stainless steel), cermet (ceramic and metal), various polymers, or other biocompatible materials. The material chosen may be matched to the material of the tissue penetrator for various properties including, for example, hardness and the like. The shuttles may be formed in any appropriate manner, including punching, progressive die, CNC, photolithography, molding, etc.

In the above examples, a pull-out force, or the force required to remove the shuttle 70 from the tissue penetrator 50, may be more than about 2 pounds of force. Preferably, the force may be about 2 to about 5 pounds. The force may be from, for example, the pulling of a suture, or suture clip or connector, attached through one of the bore holes 73 located on shuttle 70. This force should be from the direction of about the tip of the tissue penetrator.

In a preferred embodiment, illustrated in FIGS. 15A-B, the bore holes 73 are located away from channel 71 and towards the base of the triangle, which may be in a fold in the shuttle, as shown in FIG. 5B. In the other illustrated embodiments, FIGS. 6A-7 for example, the bore holes 173 are adjacent the channel. FIGS. 15A-B illustrate a position of bore holes 73 which may reduce, or even eliminate, the bending forces on the sides of shuttle 70, when suture, or the like, applies a force at bore holes 73. Typically, when bore holes 73 are located adjacent channel, as in FIG. 6A, the bending force on the side of the shuttle may peel the shuttle from the tissue penetrator 50 at a force lower than the desired removal force, due to the advantage of the force being applied to a corner of the shuttle 70. However, bore holes 73 located as shown in FIG. 5B limits this bending force, or torque, and thus prevents removal of shuttle 70 from tissue penetrator 50 at a premature time and at a force less than is desired for removal of shuttle 70.

In another embodiment, the shuttle 70 may be in the shape of a spiraled wire, or the like, such as a "finger torture" type device, whereby as the shuttle is pulled by the tissue penetrator 50, the shuttle may tighten around, thereby securing itself to the tissue penetrator. The stronger the force of the pull, the tighter the spiraled wire secures to the tissue penetrator. When the shuttle is to be transferred from the tissue penetrator, for example, to the shuttle retainer seat 25, the shuttle may be twisted, or the like, to "unlock" the shuttle from the tissue penetrator.

Other examples of shuttles 70, which may be able to clamp onto the tissue penetrator to secure itself, may be torsion springs, snap rings, a portion of wire, elastically deformable shapes, conically tapered shapes, and the like. Elastically deformable shapes may be any shape desired, such that it can be deformed to wrap around at least a portion of the tissue penetrator. Useful shapes may include, but are not limited to, cylinders, triangles, overlapping rings, and any partial portion of a shape such as a semi-circle. Once the tissue penetrator is in position, the shape of the tissue penetrator receiving area allows the elastically deformable shape to return to its original configuration while being securely attached to the tissue penetrator. Of course, the cut-out 51, or recess, or receiving area, on the tissue penetrator may in a preferred embodiment be shaped such that it coincides with the shape of the shuttle. For example, if a conically tapered shuttle were used, the tissue penetrator may include a conically tapered cut-out on a portion of the surface. The conically tapered shuttle may be deformable, and may deform upon being moved into the cut-out. Once completely within the cut-out, the conically tapered shuttle would return to its original shape and secure itself within the cut-out. The cut-out may include, for example, a lip, or the like, to assist in securing the shuttle, fully or partially, within the cut-out.

In other embodiments, the shuttle may constitute the tip of the tissue penetrator 50 itself, as illustrated and described below in reference to FIGS. 21A-22B, such that the tip may be releasably coupled on the end of the tissue penetrator. Thus, the tip of the tissue penetrator may be passed between distal opening formed by the distal end regions of the arms of the suture passer device, and to pass the suture (attached to the tip), back and forth through the tissue.

Suture 90 may, in one embodiment, be attached directly to shuttle 70 at bore hole 73, or other like retention location. Of course, suture need not be secured only by a bore hole. Instead, suture may be secured to shuttle by adhesive, a clamp, by being ties or engaged to a portion of the shuttle, or in any other suitable manner.

Additionally, suture 90 may be secured to shuttle 70 via an intermediary device, such as the examples shown in FIG. 20. One such intermediary device may be a suture clip, loop, or suture retainer 80. A suture clip allows for simple and efficient releasable connection of a suture to a shuttle. A suture clip may be used for continuous suture passing, or alternatively for single passing of a suture.

In operation, suture clips 80, such as the example illustrated in FIG. 20, may be used as part of a system for suturing tissue, particularly when used with a continuous suture passer 10. For example, a suture 90 may be passed from the second arm 20 to the first arm 21 and/or back from the first arm to the second arm of a suture passer. This may be accomplished using an extendable tissue penetrator 50 that is connected to the first arm, as described above. The extendable tissue penetrator can pierce the tissue, and can also engage a suture shuttle 70, to which a suture is attached through the suture clip 80, loop, or other attachment. The suture may then be pulled through the passage that the tissue penetrator forms in the tissue. Extending the tissue penetrator forms a passage through the tissue, which may also pass the suture between the opening formed between the distal end regions of the first and second arms. For example, the tissue penetrator may include a suture shuttle engagement region which may be, for example, a cavity within the tissue penetrator, along the outside of the tissue penetrator, or the like, to which the suture shuttle can be releasably attached. The suture can be passed from the tissue penetrator in the first arm to or from a suture shuttle retainer seat 25 connected to the second arm. Thus, both the tissue penetrator and the suture shuttle retainer seat (shuttle dock) may be configured to releasably secure the suture, which may be attached to a suture shuttle.

In some variations, the suture clip 80 described herein may include an attachment linkage 85 to a suture shuttle 70, for example a tether, leash, lead wire, or the like, which may be configured to connect the suture clip to the shuttle. In some examples, the suture clip includes a bias, for example, a spring, for securing a linkage 85 within a snap-fit element. Alternatively, the suture clip may include a central opening through which a linkage may be threaded. This linkage can act as a spacer. In one embodiment, the linkage may be stiffly attached to the shuttle 70 such that it both spaces the shuttle from the suture and also controls the position of the shuttle based on a force exerted on the linkage. The linkage will also control the position of the suture as the shuttle is passed from one arm to the other.

Similarly, the linkage 85 may be a stiff metallic wire, a portion of suture, a flexible polymeric strand, or the like. In the example of a stiff metallic wire, the wire may be welded to the shuttle such that it may project from the shuttle in a predictable manner.

In one embodiment, illustrated in FIG. 20, the shuttle 70 may be connected to a suture clip 80 that may be a compressed loop, in which the compressed loop has an inner, generally "teardrop" shaped opening 86 that is wider in one end than the other. The suture 90 may then be threaded through the inner loop 86 such that it becomes wedged within the narrow portion of the teardrop shape. The suture may then be secured by any method known in the art such as by tying a knot or bringing the end outside of the body. The suture may also be secured solely by being wedged within the teardrop shape, which may be sufficient to secure the suture within the suture clip.

FIGS. 21A-22B illustrate examples of tissue penetrators in which a suture shuttle 2101 forms the distal tip of the tissue penetrator. For example, in FIG. 21A, the suture shuttle is an approximately three-sided (pyramidal) tissue penetrating suture shuttle that include a pointed distal tip. This tissue penetrating suture shuttle fits over the distal end region of the tissue penetrating element, as shown in FIG. 21A. The tissue penetrating suture shuttle is shown disengaged in FIG. 21B.

Figure 21C:
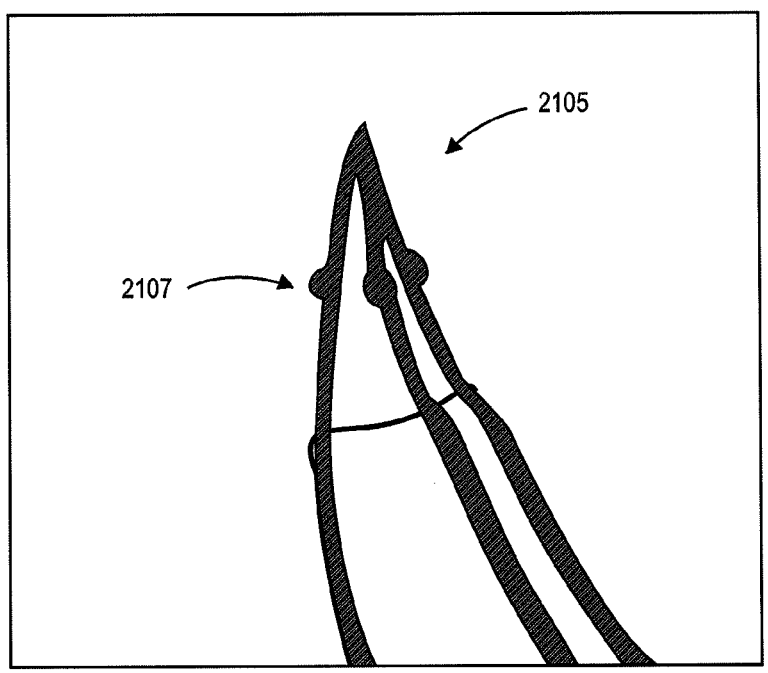
FIG. 21C shows an enlarged view of the distal tip region of the tissue penetrating element shown in FIG. 21A.

FIG. 21C shows an enlarged view of the distal tip 2105 of the tissue penetrating element of FIGS. 21A and 21B, to which the tissue penetrating suture shuttle (not visible in FIG. 21C) releasably secures. As is apparent in FIG. 21C, the sides of the distal tip region of the tissue penetrating element include one or more detents (projections) 2107 that may snap into and engage corresponding regions within the tissue penetrating suture shuttle (not shown). Thus, even without the tissue penetrating suture shuttle, the distal end of the tissue penetrating element in this example is also tissue-penetrating. In some variations, the distal end is not tissue-penetrating, but may be flattened, rounded, blunted, etc. In some variations, the distal end may be keyed to mechanically interlock with the internal portion of a tissue penetrating suture shuttle.

In some variations, the distal end of the tissue penetrating element includes one or more recesses into which a projection from the tissue penetrating suture shuttle extends.

The variation shown in FIGS. 21A-C allows the tissue penetrating suture shuttle to snap onto the distal end of the tissue penetrating member. Friction, or the elastic deformation of one or more detents, buttons, knobs, nubs, projections, etc. may be used to hold the tissue penetrating suture shuttle onto the tissue penetrating element. In some variations, the tissue penetrating suture shuttle is actively secured to the tissue penetrating element. For example, a tissue penetrating element may include a magnetic or electromagnetic element that grasps or secures the tissue penetrating suture shuttle to the distal end region of the tissue penetrating element. In some variations the tissue penetrating suture shuttle is held on the tissue penetrating element by a vacuum or other member. In some variations, a bar or other member may be extended from the tissue penetrating element to engage with a site on or within the tissue penetrating suture shuttle to lock it in position. The lock may be deactivated or withdrawn (e.g., by withdrawing a bar) in order to release the tissue penetrating suture shuttle form the tissue penetrating element.

Figure 22A:
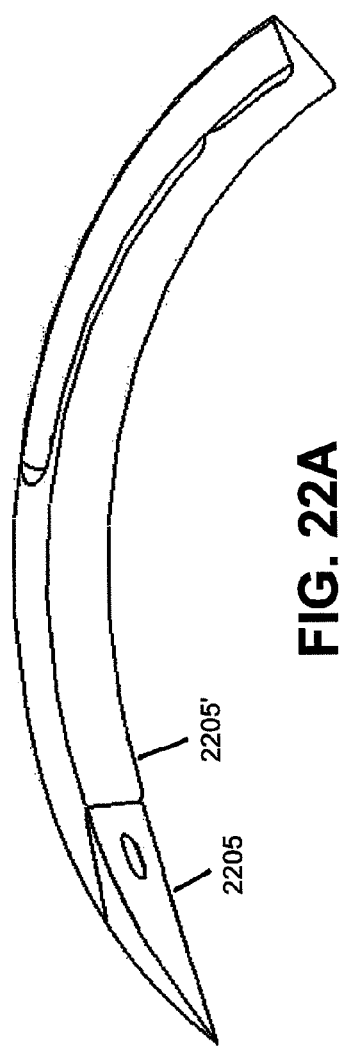
FIGS. 22A-22B show another variation of a tissue penetrating suture shuttle and tissue penetrator, in side perspective views.
Figure 22B:
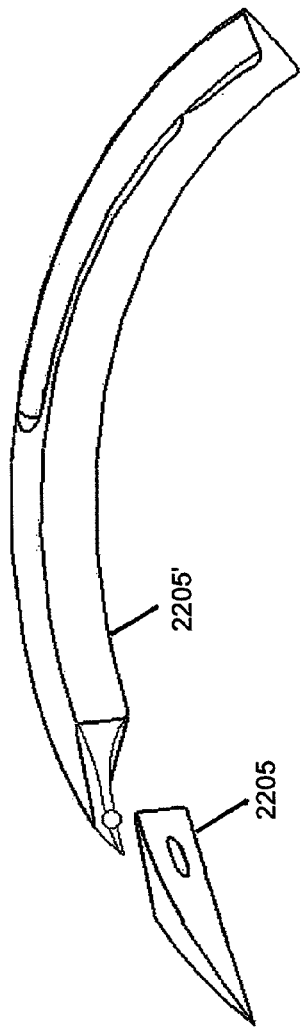

FIGS. 22A-22B illustrate another variation of a tissue penetrating suture shuttle and tissue penetrating element. In this variation, the tissue penetrating suture shuttle includes both a pointed distal end, but also includes an elongate cutting side (the bottom surface 2205, 2205'). The tissue penetrating element is also pointed at the distal end, and this end of the tissue penetrating element fits into the tissue penetrating suture shuttle. For example, FIG. 22A shows the tissue penetrating suture shuttle attached to the distal end of the tissue penetrating element. FIG. 22B shows the tissue penetrating suture shuttle disconnected from the tissue penetrating element.

In some variations the meniscus repair suture passer device is configured to pass a suture back and forth through tissue without requiring a shuttle. For example, the tissue penetrator may be configured to releasably connect directly to a suture. A tissue penetrator may include a suture engagement region (e.g., at or proximal to the distal tip of the tissue penetrator) that holds the suture until it is released into a dock on the opposite arm of the device. For example, the tissue penetrator may include a hook (with or without a latch) into which the suture may be held. In some variations the tissue penetrator includes a clamping or gasping mechanism (e.g., one or more clamping surfaces on the tip or side of the tissue penetrator) for securing the suture until it can be released into the dock on the opposite arm. Similarly, the dock (which may be present on the second or upper arm in some variations), may be adapted for directly securing the suture to the arm opposite from the arm connected to the tissue penetrator. A suture dock may be modified from the shuttle docks illustrated above, and may include a hook, clamp, gasper, or other mechanism for alternately securing the suture and releasing it onto the tissue penetrator. The dock may also include an exchange mechanism for de-coupling the suture from the tissue penetrator (e.g., releasing a latch in variations having a latch, unclamping a clamp, etc.). Thus, the dock may be configured to alternately engage and disengage the suture from the tissue penetrator and thereby release or retain it in the dock. In some variations the device may be configured to pass a suture from the second arm (where it may be pre-loaded into the dock) to the first arm (via the tissue penetrator) and then back to the second arm (again via the tissue penetrator) and released back into the dock; thus completing two passes through the tissue, which may be in different tissue locations, since the device may be repositioned between passes. In some variations additional passes through the tissue may be completed, or the device may be configured for just two passes (a forward and backward stitch).

Figure 23:
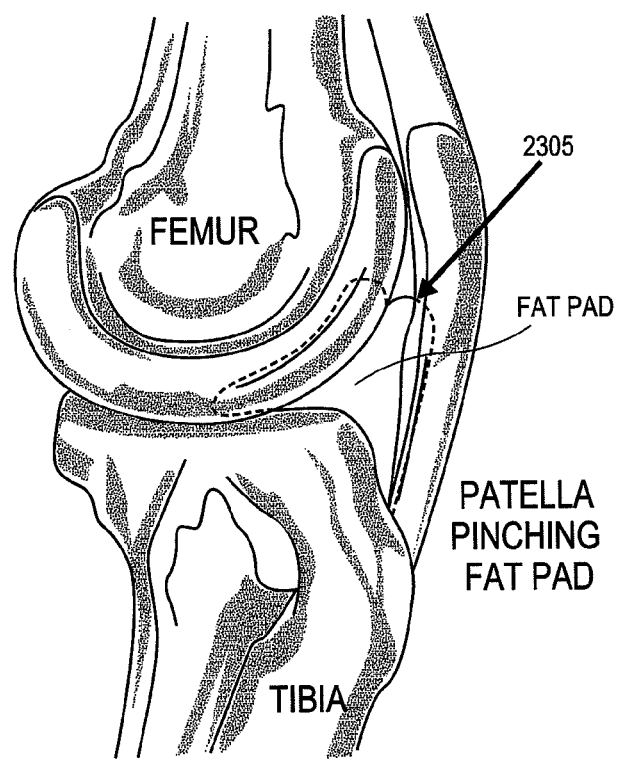
FIG. 23 illustrates a section though a knee indicating one method of approach for repairing a meniscus as described herein.

In practice, the procedure may begin with a 5-10 mm skin incision at the anterior knee through which an arthroscopy camera is inserted. The knee may then be distended with saline in typical fashion. A camera may be moved into position such that the meniscus tear can be clearly visualized. Varus or valgus stress may be placed across the knee to open up the joint space in typical fashion. FIG. 23 illustrates the anatomy referred to herein.

The meniscus repair suture passer device may then be inserted through another 5-10 mm incision created in the skin at the anterior knee. Such incisions are used for typical or accessory knee arthroscopy portals. The distal end of the device traverses the skin and enters the fat pad in the anterior compartment (see arrow 2305). Gentle pressure allows the device to slide though the fat pad and into the space between the femur and tibia. The surgeon may choose to lower his/her hand as the curved or bent distal end of the upper arm follows the curvature of the femoral condyle allowing access to the posterior or peripheral knee. The distal end region of the upper arm is then positioned approximated above the meniscus tear. In some embodiments the superior capsule may be pushed peripherally with the distal aspect of the upper arm to allow the meniscus apex to flex superiorly (illustrated in FIG. 24A-24C), thus aiding in later extension of the lower arm beneath the meniscus. The lower arm is then extended distally underneath the meniscus to be positioned.

Figure 24A:
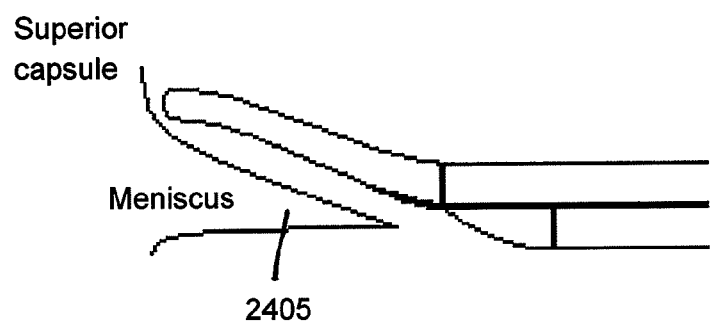
FIGS. 24A to 24C illustrate one method of positioning a meniscus repair suture passer around the meniscus.
Figure 24B:
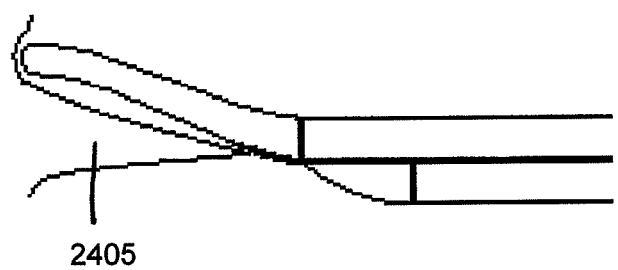
Figure 24C:
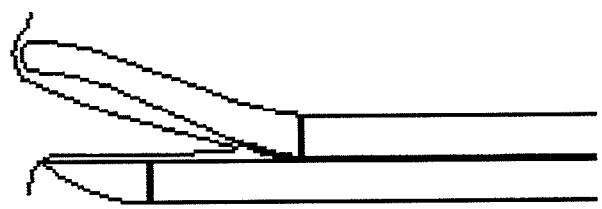

For example, in FIG. 24A-24C, the tip of the upper arm is used to apply outward pressure on the capsule just superior to the peripheral meniscus tissue. In doing so, the central aspect of the meniscus 2405 flips upward a few degrees allowing easier access for the lower arm to slide under (inferior) to the meniscus. This may allow easier exposure for the lower arm to slide under (inferior) to the meniscus and, may also permit a deeper (larger) "bite" of tissue to be obtained during the initial pass, thus more tissue can be incorporated into the repair.

In these variations, the suture may pass through both meniscus and adjacent material, all while preventing damage to vascular structures feeding the meniscus and surrounding/supporting structures. For example, peripheral tissue may be captured within the distal opening formed between the upper and lower arms of the device in a way that the suture pathway (following the tissue penetrator) arcs through the capsule behind (peripheral) to the tear during the first few needle advancements/shuttle exchanges and a second pass may then go through the meniscus tissue itself. Passing in this manner may capture the repair tissue in a way that is optimal for repair and has no risk of damaging the common peroneal nerve or popliteal artery. The arching first pass of the device may allow the capture and repair of more tissue without deleteriously plunging into the back of the knee.

Any of the variations of the shuttle passers described herein may also include suture guides, channels or controls to direct the suture as it is passed through the tissue. The suture channels may be open or closed, and may be cavities or channels that are formed within the arms, tissue penetrator(s) and intermediate regions of the device. The channels may be coated or formed to reduce friction or regions that the suture may catch or tangle on. Control of the suture may be important to the working of any of the devices described herein.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

We claim:

1. A suture passer device for passing a suture through the meniscus, the device comprising:
    an elongate body extending distally and proximally along a long axis;
    a first arm that is connected to the elongate body and axially slideable distally and proximally relative to the elongate body along the long axis,
    a second arm extending distally from the elongate body, wherein the distal region of the second arm bends away from the long axis to form a distal opening between the distal region of the second arm and the distal region of the first arm when the first arm is extended distally; and
    a tissue penetrator configured to extend across the distal opening from the first arm to the second arm to pass a suture there between, wherein the first arm is configured to retract proximally independently relative to the second arm so that it does not form the distal opening with the second arm.

2. The device of claim 1, wherein the distal end of the second arm is bendable to form an angle relative to the long axis.

3. The device of claim 1, wherein the distal end of the second arm is bendable to form an acute angle of between about 1 and 90 degrees relative to the long axis.

4. The device of claim 1, wherein the distal end of the second arm is bendable to form an acute angle of between about 20 and 50 degrees.

5. The device of claim 1, wherein the tissue penetrator is configured to releasably couple to the suture to carry the suture through a tissue.

6. The device of claim 1, wherein the distal opening is an acute-angled distal-facing opening configured to fit a meniscus therein.

7. The device of claim 1, wherein the distal opening is a v-shaped distal-facing opening configured to receive a meniscus between the second and first arms when the first arm is extended distally relative to the elongate body.

8. The device of claim 1, wherein the tissue penetrator is configured to be housed within the first arm.

9. The device of claim 1, wherein the tips of the distal ends of the second and first arms are rounded and atraumatic.

10. The device of claim 1 further comprising a proximal handle having a first control for axially moving at least the distal region of the first arm relative to the elongate body.

11. The device of claim 1 further comprising a proximal handle having a tissue penetrator control for controlling the extension and retraction of the tissue penetrator across the distal opening.

12. The device of claim 1 further comprising a dock at the distal region of the second arm configured to retain a suture, permitting the tissue penetrator to pass the suture between the first arm to the second arm.

13. The device of claim 1, wherein the tissue penetrator is configured to extend across the distal opening in a curved path.

14. The device of claim 1, further comprising a first stop to limit the movement of the first arm distally along the long axis of the device.

15. The device of claim 1, further comprising a plurality of stops at different axial positions of the first arm along the long axis.

16. A suture passer device for passing a suture through the meniscus, the device comprising:

an elongate shaft extending distally and proximally along a long axis;

a first arm that is connected to the elongate body having a distal region that is slideable distally and proximally relative to the long axis;

a second arm having a distal region configured to bend away from the long axis of the shaft at an angle to form a distal-facing opening with the first arm when the first arm is extended distally;

wherein the first arm is moveable distally and proximally relative to the second arm and wherein the first arm is configured to retract proximally independently relative to the second arm so that it does not form the distal-facing opening with the second arm;

a tissue penetrator configured to extend across the distal-facing opening from the first arm to the second arm to pass a suture there between; and a suture dock on the second arm configured to exchange the suture with the tissue penetrator.

17. The device of claim 16, wherein the second arm is bendable from a straight configuration relative to the long axis.

18. The device of claim 16, wherein the tissue penetrator is housed within the first arm and configured to extend therefrom.

19. The device of claim 16 further comprising a proximal handle having a control for axially moving at least the distal region of the first arm relative to the shaft.

20. The device of claim 16 further comprising a proximal handle having a tissue penetrator control for controlling the extension and retraction of the tissue penetrator across the distal-facing opening.

21. The device of claim 16, further comprising a first arm stop limiting the movement of the first arm along the long axis of the device.

22. A suture passer device for passing a suture through the meniscus, the device comprising:

an elongate body extending distally and proximally along a long axis;

a first arm that is connected to the elongate body and axially movable distally and proximally relative to the elongate body along the long axis, a second arm extending distally from the elongate body, wherein the distal region of the second arm is pre-bent or bendable at an angle relative to the long axis to form an angular distal-facing opening between the distal region of the second arm and the distal region of the first arm when the first arm is extended distally;

wherein the first arm is moveable distally and proximally relative to the second arm and further wherein the first arm is configured to retract proximally independently relative to the second arm so that it does not form the distal-facing opening with the second arm; and a tissue penetrator housed within the first arm that is configured to extend across the distal-facing opening to pass a suture there between.

23. The device of claim 1, wherein the tissue penetrator is further configured to bend from a straightened configuration as it extends across the distal opening.

24. The device of claim 1, wherein the tissue penetrator comprises a shape memory alloy.

25. The device of claim 1, wherein the tissue penetrator extends from a position completely within the first arm as it extends across the distal opening from the first arm to the second arm.

* * * * *